US011230587B2

(12) United States Patent
Dianzani et al.

(10) Patent No.: US 11,230,587 B2
(45) Date of Patent: Jan. 25, 2022

(54) LIGANDS OF B7H RECEPTOR IN THE TREATMENT OF OSTEOPENIA AND OSTEOPOROSIS

(71) Applicant: Università degli Studi del Piemonte Orientale "Amedeo Avogadro", Vercelli (IT)

(72) Inventors: Umberto Dianzani, Turin (IT); Casimiro Luca Gigliotti, Novara (IT); Elena Boggio, Mezzomerico (IT)

(73) Assignee: UNIVERSITÀ DEGLI STUDI DEL PIEMONTE ORIENTALE "AMEDEO AVOGADRO", Vercelli (IT)

( * ) Notice: Subject to any disclaimer, the term of this patent is extended or adjusted under 35 U.S.C. 154(b) by 241 days.

(21) Appl. No.: 15/576,789

(22) PCT Filed: May 18, 2016

(86) PCT No.: PCT/IB2016/052903
§ 371 (c)(1),
(2) Date: Nov. 24, 2017

(87) PCT Pub. No.: WO2016/189428
PCT Pub. Date: Dec. 1, 2016

(65) Prior Publication Data
US 2018/0305436 A1 Oct. 25, 2018

(30) Foreign Application Priority Data
May 27, 2015 (IT) .................. 102015000018209

(51) Int. Cl.
*C07K 14/705* (2006.01)
*A61K 38/00* (2006.01)
*A61P 19/08* (2006.01)
*A61P 19/10* (2006.01)
*G01N 33/50* (2006.01)

(52) U.S. Cl.
CPC ........ *C07K 14/70521* (2013.01); *A61K 38/00* (2013.01); *A61P 19/08* (2018.01); *A61P 19/10* (2018.01); *C07K 14/70532* (2013.01); *G01N 33/5044* (2013.01); *C07K 2319/30* (2013.01)

(58) Field of Classification Search
None
See application file for complete search history.

(56) References Cited
U.S. PATENT DOCUMENTS

| | | | |
|---|---|---|---|
| 8,389,690 B2 | 3/2013 | Tamatani et al. | |
| 2003/0022210 A1* | 1/2003 | Bonyhadi ........ | A61K 38/2013 435/6.16 |
| 2004/0146506 A1* | 7/2004 | Tamatani ............ | C07K 14/705 424/133.1 |
| 2008/0166352 A1 | 7/2008 | Siu et al. | |
| 2011/0104757 A1 | 5/2011 | Siu et al. | |
| 2012/0114595 A1* | 5/2012 | Kajihara ............ | A61K 38/177 424/85.1 |
| 2013/0171695 A1 | 7/2013 | Siu et al. | |
| 2016/0024225 A1 | 1/2016 | Hsu et al. | |
| 2016/0068600 A1 | 3/2016 | Barelle et al. | |
| 2016/0145345 A1 | 5/2016 | Siu et al. | |
| 2016/0176951 A1 | 6/2016 | Barelle et al. | |

FOREIGN PATENT DOCUMENTS

| | | |
|---|---|---|
| WO | 0046240 A2 | 8/2000 |
| WO | WO 2007/011941 | 1/2007 |
| WO | 2011020024 A2 | 2/2011 |
| WO | 2012173987 A2 | 12/2012 |
| WO | WO 2014/159725 | 10/2014 |
| WO | WO 2014/173975 | 10/2014 |

OTHER PUBLICATIONS

Jevsevar et al., 2010, Biotech. vol. 5: 113-128.*
Scott et al., 2012, vol. 12:278-287.*
Hutloff et al., 1999, Nature, vol. 397: 263-266.*
Rico et al., 1990, Clinical Rheum. vol. 9: 63-68.*
Deal, 2012, Curr Rheum. vol. 14: 231-237.*
Bottcher et al., 2008, Arth. Reas. Ther. vol. 10: 1-3.*
Duncan et al., 1965, Arhr. Rheum. vol. 8: 943-954.*
Communication pursuant to Article 94(3) EPC dated Jun. 28, 2018 in European Patent Application No. 16 727 556.9.
Gigliotti, C. L., et al.,"ICOS-Ligand Triggering Impairs Osteoclast Differentiation and Function in Vitro and in Vivo," J Immunol 197:3905-3916 (2016).
Gigliotti, C. L., et al., "B7H Triggering Inhibits Osteoclast Function in Vitro and in Vivo," EP16-Immunomodulation, Abstract: 876 (2016).
International Search Report and Written Opinion of the ISA of PCT/IB2016/052903, dated Aug. 2, 2016, 16 pages.
Hideyuki et al., "Blockade of ICOS-B7h Pathway Ameliorates Murine Collagen-Induced Arthritis", The FASEB Journal, Federation of American Societies For Experimental Biology, vol. 16, No. 4, Mar. 20, 2002, p. A713.
Occhipinti et al., "Triggering of B7h by the ICOS Modulates Maturation and Migration of Monocyte-Derived Dendritic Cells", The Journal Of Immunology, vol. 190, No. 3, Dec. 28, 2017, pp. 1125-1134.
Dianzani et al., "B7h Triggering Inhibits the Migration of Tumor Cell Lines", The Journal Of Immunology, vol. 192, No. 10, Apr. 11, 2014, pp. 4921-4931.
Dianzani et al., "B7h Triggering Inhibits Umbilical Vascular Endothelial Cell Adhesiveness to Tumor Cell Lines and Polymorphonuclear Cells", The Journal of Immunology, vol. 185, No. 7, Sep. 3, 2010, pp. 3970-3979.
Park et al.,"JAK2-STAT3 Blockade by AG490 Suppresses Autoimmune Arthritis in Mice via Reciprocal Regulation of Regulatory T Cells and Th17 Cells", The Journal of Immunology, vol. 192, No. 9, Mar. 31, 2014, pp. 4417-4424.

(Continued)

Primary Examiner — Amy E Juedes
(74) Attorney, Agent, or Firm — Nixon & Vanderhye, PC

(57) ABSTRACT

A novel use of ligands of B7h receptor in the treatment of osteoporosis or osteopenia is disclosed as well as the use of B7h receptor as target for the screening of pharmaceutical active agents useful in the treatment of osteopenia or osteoporosis.

14 Claims, 14 Drawing Sheets

Specification includes a Sequence Listing.

(56) References Cited

OTHER PUBLICATIONS

Zhang et al., "Interleukin-10 Inhibits Bone Resorption: A Potential Therapeutic Strategy in Periodontitis and Other Bone Loss Diseases", Biomed Research International, vol. 20, No. 7, Jan. 16, 2014 pp. 764-765.

Takahashi et al., "Impaired CD4 and CD8 Effector Function and Decreased Memory T Cell Populations in ICOS-Deficient Patients", The Journal of Immunology, vol. 182, No. 9, Apr. 20, 2009, pp. 5515-5527.

Swallow et al. "B7h, a novel costimulatory homolog of B7.1 and B7.2, is induced by TNF-α", *Immunity* 1999;11:423-432.

Redoglia et al. "Characterization of H4: a mouse T lymphocyte activation molecule functionally associated with the CD3/T cell receptor", Eur J Immunol 1996;26:2781-9.

Buonfiglio et al. "Characterization of a novel human surface molecule selectively expressed by mature thymocytes, activated T cells and subsets of T cell lymphomas", Eur J Immunol. 1999;29:2863-74.

Hutloff et al. "ICOS is an inducible T cell co-stimulator structurally and functionally related to CD2", Nature1999; 397:263-266.

Buonfiglio et al. "The T cell activation molecule H4 and the CD28-like molecule ICOS are identical", Eur J Immunol 2000;30:3463-7.

Di Niro et al. "Construction of miniantibodies for the in vivo study of human autoimmune diseases in animal models", BMC Biotechnology 2007;7:46.

Tomimori et al. "Evaluation of pharmaceuticals with a novel 50-hour animal model of bone loss", J Bone Miner Res. 2009;24:1194-205.

Kosuke Ebina, "Osteoporosis and its treatment in patients with rheumatoid arthritis," Clinical Rheumatology, 25:14-19, 2013.

Wang, J. et al., "Research Progress of the Correlation Between Osteoporosis and Osteoarthritis," Clin. J. Osteoporos, Mar. 2014, vol. 20, No. 3.

Iwai, H. et al., "Amelioration of Collagen-Induced Arthritis by Blockade of Inducible Costimulator-B7 Homologous Protein Costimulation," The Journal of Immunology, 2002:169-4332-4339.

* cited by examiner

A
CTR
$^{F119S}$ICOS-Fc
ICOS-Fc
ICOS-msFc
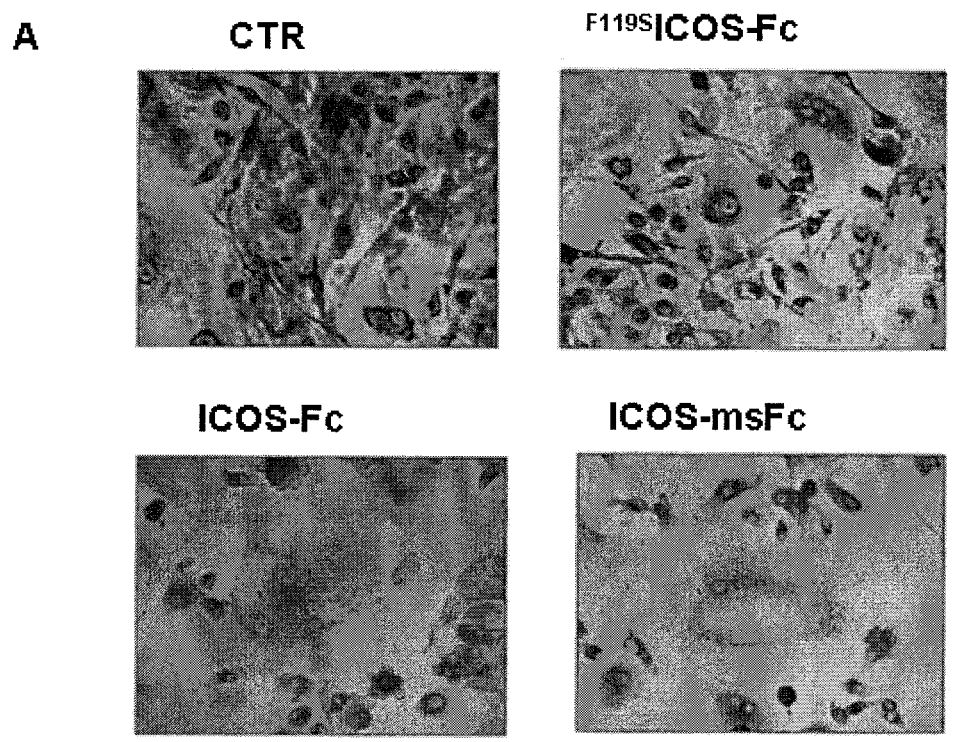
B
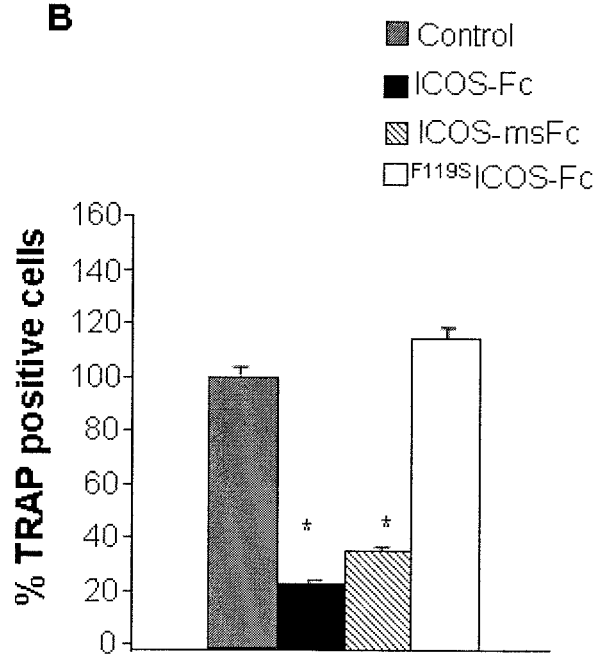
Figure 6

A
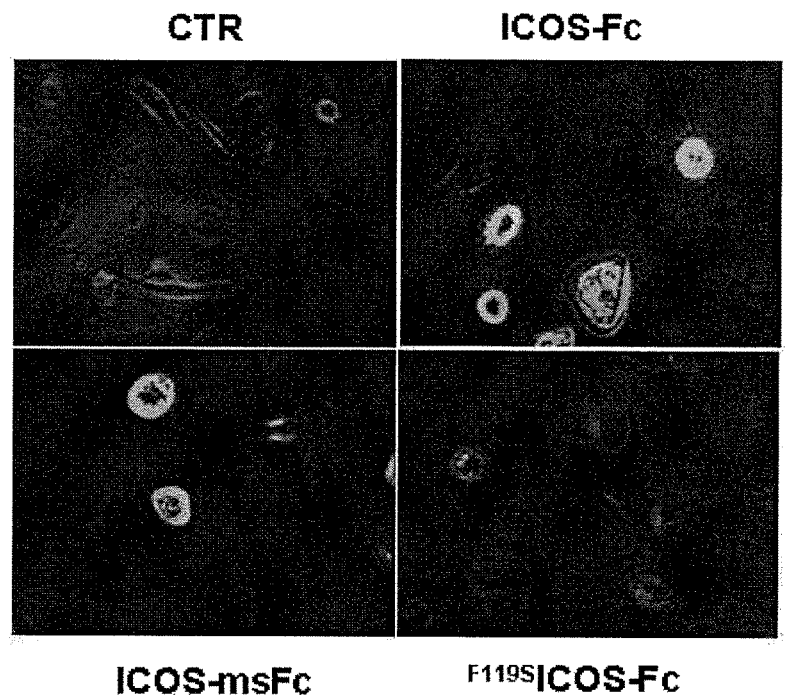
B
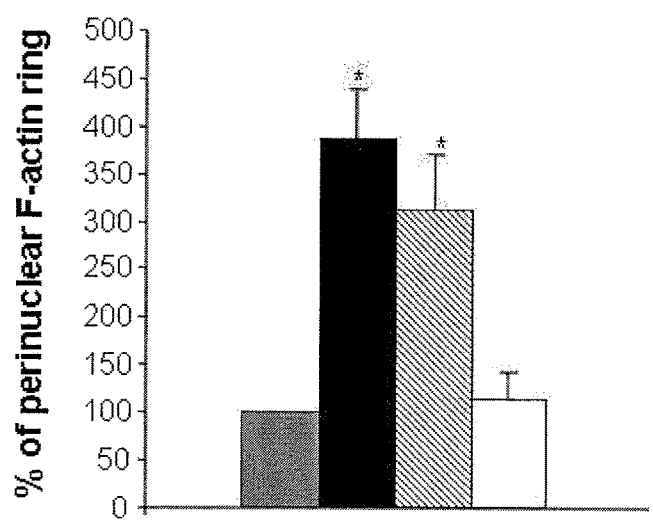
Figure 7

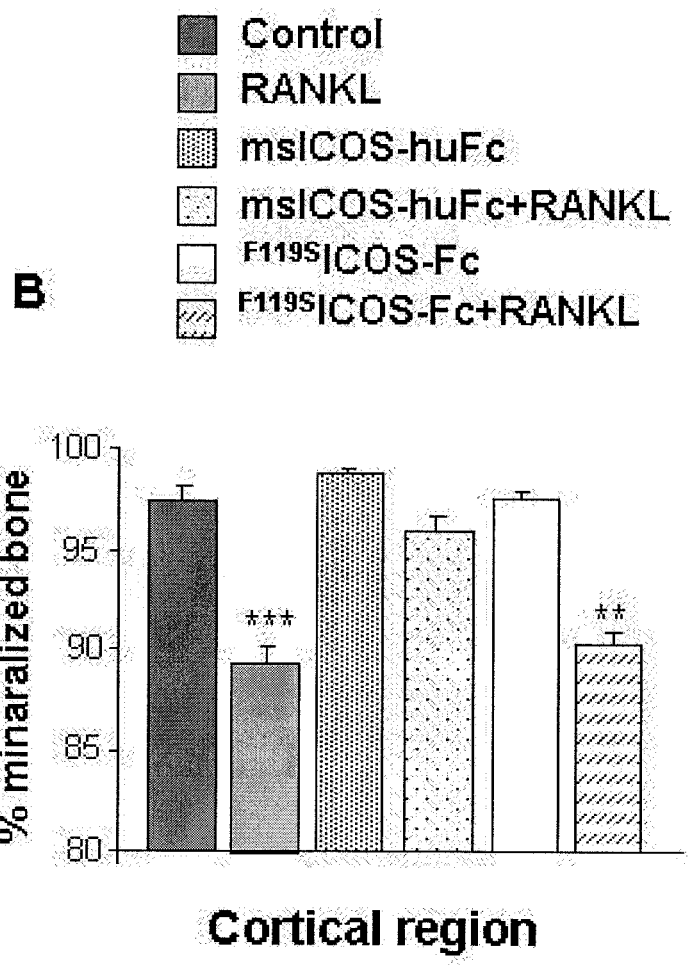
Figure 9 - cont

```
               10         20         30         40         50         60
         MGWSLILLFL VAVATGGAHA EINGSANYEM FIFHNGGVQI LCKYPDIVQQ FKMQLLKGGQ 70         80         90        100        110        120
         ILCDLTKTKG SGNTVSIKSL KFCHSQLSNN SVSFFLYNLD HSHANYYFCN LSIFDPPPFK 130        140        150        160        170        180
         VTLTGGYLHI YESQLASDKT HTCPPCPAPE LLGGPSVFLF PPKPKDTLMI SRTPEVTCVV 190        200        210        220        230        240
         VDVSHEDPEV KFNWYVDGVE VHNAKTKPRE EQYNSTYRVV SVLTVLHQDW LNGKEYKCKV 250        260        270        280        290        300
         SNKALPAPIE KTISKAKGQP REPQVYTLPP SREEMTKNQV SLTCLVKGFY PSDIAVEWES 310        320        330        340        350        360
         NGQPENNYKT TPPVLDSDGS FFLYSKLTVD KSRWQQGNVF SCSVMHEALH NHYTQKSLSL 370        380
         SPGKTSGKPI PNPLLGLDST
```

Figure 10

```
                  10         20         30         40         50
            MKSGLWYFFL FCLRIKVLTG EINGSANYEM FIFHNGGVQI LCKYPDIVQQ 60         70         80         90        100
            FKMQLLKGGQ ILCDLTKTKG SGNTVSIKSL KFCHSQLSNN SVSFFLYNLD 110        120        130        140        150
            HSHANYYFCN LSIFDPPPFK VTLTGGYLHI YESQLCCQLK FWLPIGCAAF 160        170        180        190
            VVVCILGCIL ICWLTKKKYS SSVHDPNGEY MFMRAVNTAK KSRLTDVTL
```

Figure 11

```
            10         20         30         40         50
    MRLGSPGLLF LLFSSLRADT QEKEVRAMVG SDVELSCACP EGSRFDLNDV 60         70         80         90        100
    YVYWQTSESK TVVTYHIPQN SSLENVDSRY RNRALMSPAG MLRGDFSLRL 110        120        130        140        150
    FNVTPQDEQK FHCLVLSQSL GFQEVLSVEV TLHVAANFSV PVVSAPHSPS 160        170        180        190        200
    QDELTFTCTS INGYPRPNVY WINKTDNSLL DQALQNDTVF LNMRGLYDVV 210        220        230        240        250
    SVLRIARTPS VNIGCCIENV LLQQNLTVGS QTGNDIGERD KITENPVSTG 260        270        280        290        300
    EKNAATWSIL AVLCLLVVVA VAIGWVCRDR CLQHSYAGAW AVSPETELTG
```

Figure 12

LIGANDS OF B7H RECEPTOR IN THE TREATMENT OF OSTEOPENIA AND OSTEOPOROSIS

This application is the U.S. national phase of International Application No. PCT/IB2016/052903 filed May 18, 2016, which designated the U.S. and claims priority to Italian Application No. 102015000018209 filed May 27, 2015, the entire contents of each of which are hereby incorporated herein by reference.

FIELD OF THE INVENTION

The present invention concerns a novel use of ligands of B7h receptor in the treatment of osteopenia and osteoporosis.

BACKGROUND OF THE INVENTION

Osteoclasts are giant cells formed by cell-cell fusion of monocyte-macrophage precursors and characterized by multiple nuclei, abundant vacuoles and lysosomes; they play a key role in bone development and remodelling, which involves also osteoblasts and osteocytes. Osteoclasts differentiate from monocytes under the influence of macrophage colony stimulating factor (M-CSF) and receptor activator of nuclear factor k-B ligand (RANKL).

Osteoclasts function is stimulated by triggering of receptor activator of nuclear factor-kappa B (RANK) expressed on the membrane of osteoclasts by RANKL. In the healthy bone, the main source of RANKL are osteoblasts expressing it as a surface receptor in response to bone-resorbing factors and it is cleaved into a soluble molecule (sRANKL) by metalloproteinase (MMPs). Moreover, RANKL is expressed also by stromal cells, lymphocytes, and macrophages which can support osteoclasts function during inflammation. Osteoprotegerin (OPG) is a soluble receptor of RANKL and is secreted by osteoblasts and stromal cells to inhibit RANK stimulation and osteoclastogenesis induced by RANKL. The binding of M-CSF to its colony-stimulating factor 1 receptor (c-fms) on osteoclasts progenitors upregulates expression of RANK in these cells and promotes osteoclastogenesis. Osteoclasts differentiation includes cell polarization with formation of ruffled membrane and sealing of the osteoclasts to the bone to form a sealing zone, or clear zone, that separates the resorption lacunae from the surround. This is the secretion site of acid, tartrate resistant acid phophatase (TRAP), cathepsins, and MMPs leading to demineralization of the inorganic component of the bone and hydrolysis of its organic components. Then, coupling mechanisms promote the differentiation and recruitment of osteoblasts at the resorption lacunae, where they secrete the organic component of bone which is then mineralized by hydroxyapatite. Some osteoblasts entrapped within the matrix become osteocytes and secrete sclerostin inhibiting osteoblasts function and terminating the remodelling cycle. Sclerostin expression is inhibited when osteocytes are exposed to mechanical forces, which targets bone remodeling to areas of maximal strain.

An excess of osteoclasts activity leads to pathological bone loss and can be detected in conditions such as osteoporosis, rheumatoid arthritis and other autoimmune diseases, in which a key role has been ascribed to inflammatory cytokines and adaptive immunity. Moreover, some neoplasia involving immune cells, such as multiple myeloma, are characterized by intense focal bone erosions ascribed to high expression of RANKL by stromal cells and, possibly, myeloma cells. Bone metastases of solid cancer, too, may be osteolytic and prostatic cancer may promote bone resorption through the expression of a soluble form of RANKL.

Several inflammatory cytokines, such as TNF-α, Interleukin (IL)-1, IL-6, and M-CSF upregulate RANKL expression and stimulate osteoclasts function. A key role is played by type 17 T helper (Th17) cells secreting IL-17 that induces the expression of RANKL in osteoblasts and synovial cells. Moreover, IL-17 supports recruitment of several types of immune cells which contribute to the bone damage and produce cytokines and other proinflammatory molecules supporting osteoclasts differentiation and activity.

B7h (CD275, also known as B7H2, B7-RP1, ICOSL, GL50) belongs to the B7 family of surface receptors and it binds ICOS (CD278), which belongs to the CD28 family[1-5]. ICOS is selectively expressed by activated T cells, whereas B7h is expressed by a wide variety of cell types, including B cells, macrophages, dendritic cells, and a subset of T cells. However, B7h is also expressed by cells of non haemopoietic origin such as vascular endothelial cells, epithelial cells, and fibroblasts, and in many primary tumors and tumor cell lines. The main known function of B7h is triggering of ICOS, which functions as a costimulatory molecule for activated T cells by modulating their cytokine secretion and, particularly, increasing secretion of Interferon (IFN)-γ (in humans), IL-4 (in mice), and IL-10, IL-17, and IL-21 (in both species). However, recent reports have shown that the B7h:ICOS interaction can trigger bidirectional signals able to modulate also the response of the B7h-expressing cells. In mouse dendritic cells, this B7h-mediated "reverse signalling" induces partial maturation with prominent augmentation of IL-6 secretion. In human dendritic cells, it was found that it modulates cytokine secretion, promotes capacity to cross-present endocytosed antigens in class I MHC molecules, and inhibits adhesiveness to endothelial cells and migration. B7h stimulation also inhibits adhesiveness and migration of endothelial cells and tumor cell lines. These effects are accompanied by decreased phosphorylation of ERK and p38 in endothelial cells; decreased phosphorylation of FAK and down-modulation of β-Pix in endothelial cells and tumor cells. Finally, B7h triggering inhibits development of lung metastases upon injection of NOD-SCID-IL2Rγnull mice with CF-PAC1 cells, and C57BL/6 mice with B16-F10 cells.

OBJECT AND SUMMARY OF THE INVENTION

The present description concerns expression of B7h receptor in osteoclasts and B7h receptor triggering to reduce and/or inhibit osteoclasts differentiation, maturation and/or activity.

The object of the present invention is to provide new compounds for the treatment of osteoporosis or osteopenia.

According to the invention, the above object is achieved thanks to the method specified in the ensuing claims, which are understood as forming an integral part of the present description.

In an embodiment, the instant disclosure discloses a novel use of ligands of B7h receptor in the treatment of osteoporosis and osteopenia.

In a further embodiment, the present description concerns use of B7h receptor as target for the screening of pharmaceutical active agents useful in the treatment of osteopenia and osteoporosis, wherein the pharmaceutical active agent interferes with osteoclasts differentiation, maturation and/or function, thus inhibiting osteoclastogenesis.

BRIEF DESCRIPTION OF THE DRAWINGS

The invention will now be described, by way of example only, with reference to the enclosed figures of drawing, wherein:

FIG. 6: Effect of ICOS-Fc on TRAP staining. MDOCs differentiating from monocytes were treated with or without ICOS-Fc (1 µg/ml), ICOS-msFc (1 µg/ml), or $^{F119S}$ICOS-Fc (1 µg/ml) as described in FIG. 2 ($T^{14-21}$ treatment). At day 21, the cell layer was stained with the Fast Garnet GBC Base Solution assessing TRAP activity. A) Microphotographs of the staining area were taken to monitor the TRAP positive cells (n=3). B) The bar graphs show the % of the TRAP$^+$ cells; data are expressed as the mean±SEM of the percentage of inhibition versus the control from 3 independent experiments (*: $p<0.01$ versus the control).

FIG. 7: Effect of B7h triggering on actin remodelling. MDOCs differentiating from monocytes were treated with or without ICOS-Fc (1 µg/ml), ICOS-msFc (1 µg/ml), or $^{F119S}$ICOS-Fc (1 µg/ml) as described in FIG. 2 ($T^{14-21}$ treatment). A) Cells were stained with fluorescein isothiocyanate (FITC)-phalloidin marking actin and were photographed by a fluorescent microscope at Day 21. B) The bar graphs show the % of the perinuclear F actin ring positive cells; data are expressed as the mean±SEM of the percentage of increase versus the control from 3 independent experiments (*: $p<0.05$ versus the control).

FIG. 10: Amino acid sequence of ICOS-Fc construct (SEQ ID No. 1).

FIG. 11: Amino acid sequence of human ICOS (SEQ ID No. 29); the underlined amino acids correspond to the extracellular portion of ICOS (SEQ ID No. 2).

FIG. 12: Amino acid sequence of human B7h receptor (SEQ ID No. 27).

DETAILED DESCRIPTION OF THE INVENTION

Figure 1:
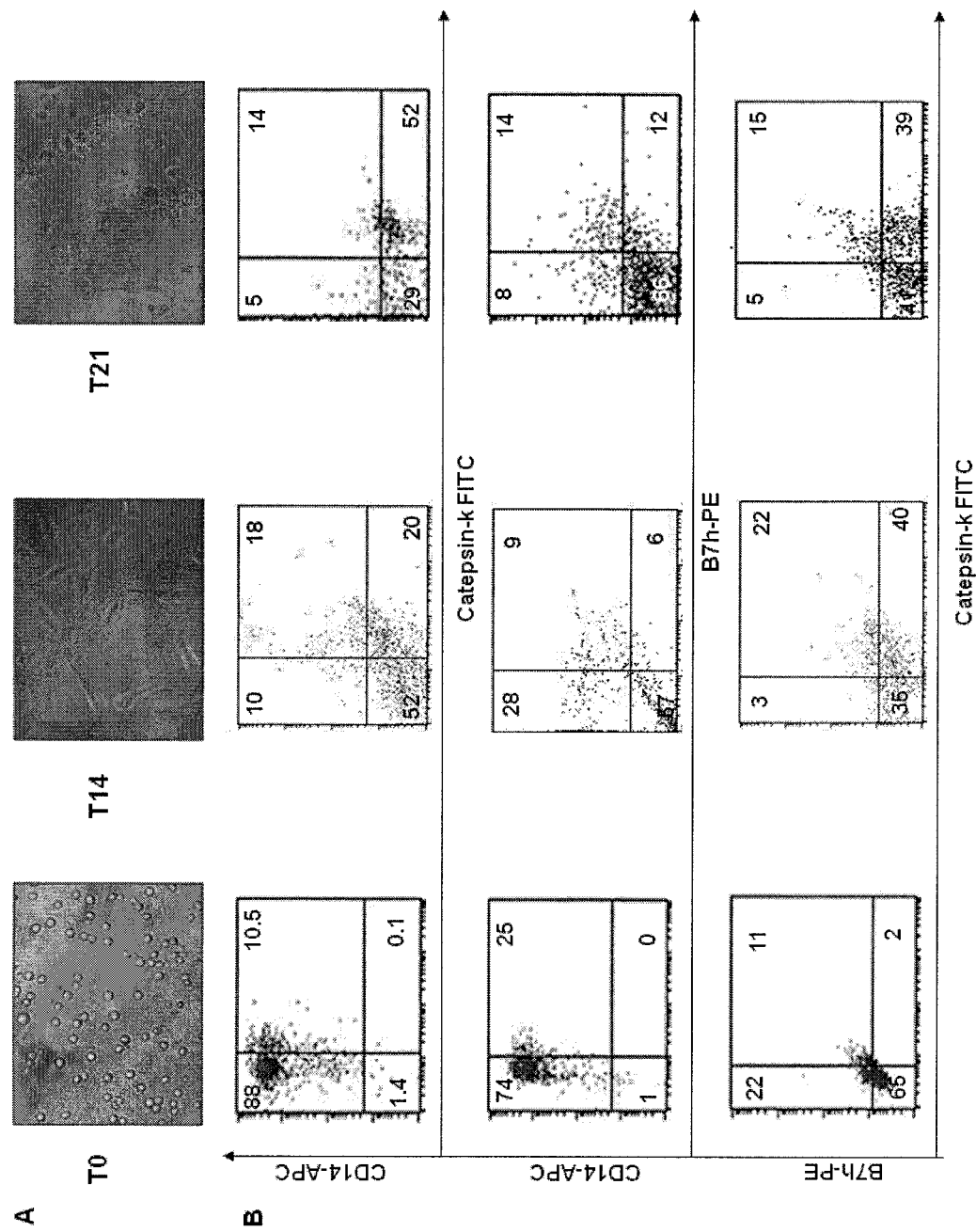
FIG. 1: Morphological analysis and CD14, B7h, and Catepsin-K expression in monocytes-derived osteoclasts (MDOCs). A) Cells were photographed at day 0 (T0), day 14 (T14) and day 21 (T21) of culture in the presence of M-CSF (25 ng/ml) and RANKL (30 ng/ml) by phase-contrast microscopy. B) CD14, B7h, and Catepsin-K expression were assessed by flow cytometry in MDOCs at T0, T14 and T21. Numbers in each panel indicate the % of positive cells. Panels are representative of 5 experiments.

The invention will now be described in detail, by way of non limiting example, with reference to a novel use of ICOS, natural ligand of B7h receptor, for the treatment of osteoporosis and osteopenia.

It is clear that the scope of this description is in no way limited to the use of ICOS only; other ligands of B7h receptor (like for example antibodies, either monoclonal antibodies, and genetically engineered/humanized antibodies and fragments thereof) may be used in the treatment of osteoporosis and osteopenia, wherein such ligands are able to reduce/inhibit osteoclasts differentiation, maturation and/or function thus inhibiting bone loss induced by osteoclasts being able to trigger B7h receptor activity in osteoclasts.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The present description concerns a novel use of ligands of B7h receptor in the treatment of osteoporosis and osteopenia, such ligands being able to trigger/stimulate B7h receptor activity, preferably in osteoclasts.

In an embodiment, the ligand of B7h receptor useful in the treatment of osteoporosis and osteopenia is selected from:
a) a human ICOS protein having the amino acid sequence set forth in SEQ ID No. 29;
b) a homologue of human ICOS protein having at least 80%, preferably at least 90% sequence homology to the amino acid sequence set forth in SEQ ID No. 29;
c) a human ICOS portion of the amino acid sequence set forth in SEQ ID No. 29 having the ability of binding to B7h receptor and inhibiting osteoclasts differentiation, maturation and/or function of native ICOS protein;
d) a human ICOS extracellular domain having the amino acid sequence set forth in SEQ ID No. 2;
e) a human ICOS extracellular domain portion of the amino acid sequence set forth in SEQ ID No. 2 having the ability of binding to B7h receptor and inhibiting osteoclasts differentiation, maturation and/or function of the amino acid sequence set forth in SEQ ID No. 2; or
f) a homologue of human ICOS extracellular domain having at least 80%, preferably at least 90% sequence homology to the amino acid sequence set forth in SEQ ID No. 2 and having the ability of binding to B7h receptor and inhibiting osteoclasts differentiation, maturation and/or function of the amino acid sequence set forth in SEQ ID No. 2.

In an embodiment, the present description concerns use of B7h receptor as target for the screening of pharmaceutical active agents useful in the treatment of osteopenia and osteoporosis, wherein the pharmaceutical active agent interferes with osteoclasts differentiation, maturation and/or function, binds to B7h receptor and triggers B7h receptor activity.

In a further embodiment, the present description provides a pharmaceutical composition for use in the treatment of osteoporosis and osteopenia comprising at least one ligand of B7h receptor and a pharmaceutical acceptable vehicle.

In an embodiment, the pharmaceutical composition comprises at least one ligand of B7h receptor selected from:
a) a human ICOS protein having the amino acid sequence set forth in SEQ ID No. 29;
b) a homologue of human ICOS protein having at least 80%, preferably at least 90% sequence homology to the amino acid sequence set forth in SEQ ID No. 29;
c) a human ICOS portion of the amino acid sequence set forth in SEQ ID No. 29 having the ability of binding to B7h receptor and inhibiting osteoclasts differentiation, maturation and/or function of native ICOS protein;
d) a human ICOS extracellular domain having the amino acid sequence set forth in SEQ ID No. 2;
e) a human ICOS extracellular domain portion of the amino acid sequence set forth in SEQ ID No. 2 having the ability of binding to B7h receptor and inhibiting osteoclasts differentiation, maturation and/or function of the amino acid sequence set forth in SEQ ID No. 2; or
f) a homologue of human ICOS extracellular domain having at least 80%, preferably at least 90% sequence homology to the amino acid sequence set forth in SEQ ID No. 2 and having the ability of binding to B7h receptor and inhibiting osteoclasts differentiation, maturation and/or function of the amino acid sequence set forth in SEQ ID No. 2.

In a still further embodiment, the present description provides a method of identifying a pharmaceutical active agent suitable for use in the treatment of osteopenia and osteoporosis, comprising the steps of: a) providing a test agent, b) putting in contact the test agent with osteoclasts expressing B7h receptor, c) testing the ability of the test agent to reduce osteoclasts maturation, differentiation and/or function, d) selecting the test agent that reduces osteoclasts maturation, differentiation and/or function as the active agent useful in the treatment of osteopenia and osteoporosis, wherein the active agent binds to B7h receptor and triggers B7h receptor activity. Preferably, the method provides for measuring secretion of tartrate-resistant acid phosphatase (TRAP) by osteoclasts, cell actin cytoskeleton organization in osteoclasts, and/or calcium release by osteoclasts.

In a different embodiment, the present description concerns a method of treating osteoporosis or osteopenia comprising the steps of: providing a patient suffering from osteoporosis or osteopenia, administering to the patient a medicament comprising a ligand of B7h receptor, thereby reducing osteoporosis or osteopenia in the patient.

Bone remodelling is a complex process managed by osteoblasts and osteoclasts, and the immune system is involved in regulating the function of these cells through the activity of cytokines and surface receptors.

The present description discloses a novel pathway involved in the lymphocyte/bone cell interactions by showing that binding of ICOS, expressed by activated T cells, to its ligand B7h, expressed by osteoclasts, inhibits osteoclasts maturation and function. These effects were detected using ICOS-Fc, a recombinant soluble form of ICOS, and were specific since they were not displayed by $^{F119S}$ICOS-Fc, a mutated form of ICOS-Fc incapable of binding B7h.

The effect on osteoclasts differentiation was detected by treating cells with ICOS-Fc during the in vitro differentiation of monocytes to osteoclasts driven by M-CSF and RANKL. ICOS-Fc almost completely blocked the differentiation when treatment was started at the beginning of the three weeks differentiating culture, but it arrested the differentiation also when the treatment was started in the last week, as shown by the decreased cell multinuclearity and the arrest of acquirement of the osteoclasts morphologic and phenotypic features induced by treatment with ICOS-Fc. This effect was not due to cell toxicity since cell survival was normal even when cultures were prolonged for a fourth week.

Moreover, the effect was reversible since interruption of the treatment in the last week of culture allowed cells to restart the osteoclasts differentiation path. The arrest of differentiation was accompanied by an altered organization of the actin cytoskeleton which, in ICOS-Fc treated cells, displayed a perinuclear distribution in a F-acting ring without the signs of polarization typical of the sealing zone delimiting the erosive lacuna detected on osteoclasts. In line with these data, cells treated with ICOS-Fc displayed decreased expression of TRAP and decreased osteolytic activity in vitro.

A second key point was the effect of ICOS-Fc on already differentiated osteoclasts, in which treatment with ICOS-Fc induced a striking decrease of the cell and nuclei sizes without substantial effects on cell viability. Again, the effect was reversible since cells reenlarged and reassumed the osteoclasts phenotype upon interruption of the treatment.

These effects on in vitro osteoclasts differentiation and function were supported by the in vivo results showing that treatment with ICOS-Fc strikingly inhibits the systemic bone resorption induced in mice by treatment with high doses of soluble RANKL, which is a mouse model of osteoporosis comparable to the ovariectomy model in terms of decrease in bone density.

The immune system is capable to modulate bone formation, and bone loss is a common feature of several chronic inflammatory and autoimmune diseases. Indeed, the risk of osteoporosis is increased in patients with rheumatoid arthritis, inflammatory bowel disease or systemic lupus erythematosus, and aggressive localized bone destruction can be a feature of certain autoimmune diseases, cancers, and infections.

Rheumatoid arthritis patients display three types of bone involvement: osteoporosis, periarticular bone loss, and joint erosions. Periarticular bone loss and joint erosions are specific of rheumatoid arthritis and involve the sites hit by the autoimmune response. Inflammatory cytokines such as IL-1, IL-6 and TNF-α are abundant in the synovial fluid and synovium and can induce RANKL on synovial fibroblasts and stromal cells. Moreover, RANKL is expressed by T and B cells in the synovial tissue and fluid of rheumatoid arthritis patients and can be involved in osteoclasts activation, and antibodies against citrullinated proteins, which are a rheumatoid arthritis marker, may have a stimulating effect on osteoclasts. By contrast, osteoporosis is not specific of rheumatoid arthritis but is a common finding in chronic inflammatory diseases such as psoriasis, ankylosing spondylitis, systemic lupus erythematosus, multiple sclerosis, inflammatory bowel diseases, pemphigus vulgaris, and others. It is also typical in chronic inflammation associated with transplantation and aging. In chronic inflammation, osteoporosis is ascribed to multiple factors including high levels of inflammatory cytokines in the blood and, often, steroid therapy.

Menopausal estrogen deficiency may involve increased osteoclasts activity due to removal of an inhibitory effect of estrogens on osteoclasts differentiation and function, but also increased production of inflammatory cytokines such as TNF-α and IL-17 and increased RANKL expression of B and T cells.

In the immune control of bone formation, a key role has been ascribed to T helper cells. Th1 and Th2 cells secrete IFN-γ and IL-4, respectively, which are anti-osteoclastogenic cytokines. By contrast, Th17 cells express high levels of RANKL and secrete IL-17 inducing expression of RANKL on mesenchymal cells and recruitment of inflammatory cells. Moreover, Th17 cells secrete also IL-22 that may induce osteoblast differentiation enhancing bone formation at sites of inflammation. The cells may act also by use of surface receptors since their CD40L can stimulate CD40 on stromal cells inducing these cells to express RANKL and suppressing expression of OPG downregulating the activity of the RANKL/RANK axis. Moreover, osteoclastogenesis can be inhibited also by regulatory T cells (Treg) through release of transforming growth factor β (TGFβ) and surface expression of cytotoxic T lymphocyte antigen 4 (CTLA4) that is capable to inhibit osteoclasts formation by binding its ligands B7.1 and B7.2 expressed on monocytes and preventing their differentiation to osteoclasts. This finding is intriguing since both CTLA4 and ICOS belong to the CD28 family of costimulatory receptors and bind surface receptors belonging to the B7 family. Moreover, ICOS too is involved in Treg function since, in appropriate conditions, ICOS triggering can induce Treg differentiation and TGFβ secretion from naïve Th cells, and subsets of Treg cells express high levels of ICOS. The effect displayed by B7h triggering on osteoclasts seems to be wider than that displayed by B7.1/B7.2 triggering since it also reversibly inhibits the function of differentiated osteoclasts.

Human B7h receptor has the amino acid sequence set forth in SEQ ID No. 27.

Human ICOS protein, the natural ligand of B7h receptor, has the amino acid sequence set forth in SEQ ID No. 29.

The ligands of B7h receptor useful for the treatment of osteoporosis and osteopenia can be selected from the ligands of B7h receptor of natural, synthetic, or recombinant origin, like for example ICOS or portions thereof, small molecule compounds, aptamers, antibodies, peptides, B7h receptor dominant positive, wherein such ligands bind to B7h receptor and are able to trigger B7h receptor activity.

The ligands of B7h receptor may be fused or conjugated to one or more stabilizing molecules in order to reduce or prevent degradation, to increase half-life and/or solubility, to reduce toxicity, and/or immunogenicity.

Use of molecules able to stabilize a protein for its administration to a mammal is a technique widely known in the art.

The B7h receptor ligand may be conjugated to an antibody or an antibody fragment in order to increase specificity, pharmacokinetics, and/or biodistribution, exploiting the antibody properties of specifically binding to an osteoclast or another bone component.

Stabilizing molecules that can be conjugated to a B7h receptor ligand can be selected i.a. from:

Polyethylene glycols (PEGs) or derivatives thereof. PEG derivatives able to link amino groups present on the B7h receptor ligands are i.a. epoxide PEG, aldehyde PEG, nitrophenyl carbonate PEG and succinimidyl ester PEG; PEG derivatives able to link thiol groups present on the B7h receptor ligands are i.a. orthopyridyl disulfide PEGs; PEG derivatives able to link hydroxyl groups present on the B7h receptor ligands are i.a. PEG-COOH activated with N-hydroxysuccinimide or hydroxybenzotriazole. Other PEG derivatives are represented by PEG-polyacetal with pH-dependent hydrolysis, and PEG-dextrin (polymer-masking-unmasking-protein therapy, PUMPT).

poly-L-lysine citramide (via a lysine or an ethylcarbamate spacer), styrenemaleic acid anhydride and poly-hydroxypropylmetacrylamide.

human Fc antibody domain.

In order to increase the delivery of the B7h receptor ligand to the site of treatment, namely osteoclasts expressing B7h receptor, the B7h receptor ligands may also be hyperglycosylated or conjugated to mannose residues.

Hyperglycosylation may be performed by either in situ chemical reactions or site-directed mutagenesis resulting in either N-linked or O-linked protein glycosylation. In N-linked glycosylation, the saccharide chain is attached to asparagine of tripeptide sequence Asn-X-Ser/Thr, where X represents an amino acid other than proline. Polysialic acid (PSA) is often used for hyperglycosylation. Large-molecular-weight PSAs are suitable for the delivery of low-molecular-weight drugs and peptides, while lower molecular weight PSAs could be used for large proteins as well as particulate drug-delivery systems.

The conjugation to mannose residues exploits binding of the conjugate to mannose receptors, which are reported to be expressed on Kupffer cells, macrophages, alveolar, monocyte-derived dendritic cells and subsets of vascular and lymphatic endothelial cells. Mannosylated proteins can be recognized by mannose-specific lectins, namely, mannose receptors and MBPs.

The delivery of B7h receptor ligand may also be increased exploiting colloidal drug delivery systems known in the art, wherein the colloidal carriers can be selected i.a. from microparticles, nanoparticles and liposomes. Microparticles are generally made of biodegradable polymers like for example starch, alginate, collagen, poly(lactide-co-glycolide) (PLGA), polycaprolactones (PCL). Nanoparticles are usually manufactured from natural or synthetic polymers, such as chitosan, alginate, PCL, polylactic acid (PLA), poly(glycolide), PLGA. Liposomes may also be surface modified with PEG in order to interfere with recognition and uptake by reticulo endothelial system and to extend circulation time. Moreover, in situ thermosensitive hydrogels undergo sol-gel phase transition in response to changes in temperature.

Materials and Methods

Cells

Peripheral Blood Mononuclear Cells (PBMCs) were obtained by density gradient centrifugation from human blood samples obtained from healthy donors who signed their written informed consent. Osteoclasts were prepared from $CD14^+$ monocytes, isolated from PBMCs with the EasySep™ Human CD14 Negative Selection Kit (cod. 19059, StemCells Techologies, Vancouver, BC, Canada). In particular, $0.5\times10^6$ monocytes were plated in a 24 wells plate (cod. 662160, Greiner Bio-One, Capital DriveMonroe, N.C., USA) and cultured for 21 days in differentiation medium, composed of DMEM (cod. 41966-029 Invitrogen, Burlington, ON, Canada, USA), and 10% Fetal Bovine Serum (FBS; cod. 10270, Invitrogen), supplemented with recombinant human M-CSF (25 ng/ml, cod. 216-MC, R&D Systems, Minneapolis, Minn., USA), and RANKL (30 ng/ml, cod. 390-TN, R&D Systems). The differentiation medium was changed every 3 days. At different times, cells were treated with 1 μg/ml of either ICOS-Fc (SEQ ID No. 1—a fusion protein containing the extracellular portion of the human ICOS (SEQ ID No. 2)) fused to the human IgG1 Fc (SEQ ID No. 3)) or ICOS-msFc (SEQ ID No. 4—a chimeric molecule containing the extracellular portion of the human ICOS (SEQ ID No. 2) fused to the mouse IgG1 Fc (SEQ ID No. 5)). Controls were performed using $^{F119S}$ICOS-Fc (SEQ ID No. 6—wherein the mutated form of the extracellular portion of the human ICOS (SEQ ID No. 7) carrying the F119S substitution is fused to the human IgG1 Fc (SEQ ID No. 3)) and msICOShuFc (SEQ ID No. 24—a fusion protein containing the extracellular portion of the mouse ICOS (SEQ ID No. 28)) fused to the human IgG1 Fc (SEQ ID No. 3)).

ICOS Cloning and Production

The extracellular portion of the human or mouse ICOS was cloned into a modified eukaryotic expression vector derived from pCDNA3.1/Hygro(+) plasmid (cod. V870-20, Invitrogen) and reported as p-Minibody (pMB-SV5) by Di Niro R. et al.[6], PubMed ID: 17678525. This vector differs from the original one by: the Kozak sequence (5' CCACATGG 3'-SEQ ID No. 8) which is required for the initiation of the translation in eukaryotic cells; the secretory leader sequence (5' GCTGGAGCCTGATCCTCCTGTTCCTCGTCGCTGTGGCTACA 3'-SEQ ID No. 9) which was introduced to allow the release of the protein in the culture supernatants; the mini intron sequence (5'GTAAGGGGCTCACAGTAGCAGGCTTGAGGTCTGGACATATATATG GGTGACAATGACATCCACTTTGCCTTTCTCTCCACAG 3'-SEQ ID No. 10) to increase the level of the protein expression. A tag sequence to target the produced-protein was introduced and it is derived from Simian Virus-5 (SV5 tag) (5' GGCAAACCAATCCCAAACCCACTGCTGGGCCTGGATAGTACT 3'-SEQ ID No. 11) and it is useful for monoclonal antibody recognition of the protein. This vector allowed to clone the fragments of interest in frame with the coding sequence of the human or mouse constant fragment of the immunoglobulin IgG1 (Fc) domain, having nucleotide sequences set forth in SEQ ID No. 30 and 31, respectively.

To generate the ICOS-Fc construct (SEQ ID No. 1), the nucleotide sequence encoding the extracellular portion of the human ICOS (SEQ ID No. 12) was amplified with specific primers:

```
ICOS forward BsshII primer
(5' GGCGCGCATGCCGAAATCAATGGTTCTGCC 3'-
SEQ ID No.: 13,
```

Sigma-Genosys, The Woodlands, Tex., USA) and ICOS reverse NheI primer

```
(5' GCTAGCAAGTTGTGATTCATAAATATGC 3'-
SEQ ID No.: 14,
```

Sigma-Genosys). The amplified fragments were digested with BssHII (cod. R0199S, New England Biolabs inc, Ipswich, Mass., USA) and NheI (cod. R0131S, New England Biolabs inc) enzymes. The double digested fragments were cloned into the previously described pMB-SV5 plasmid. The nucleotide sequence was determined by sequencing.

The nucleotide sequence of the expression vector coding for ICOS-Fc is set forth in SEQ ID No. 21.

In the case of ICOS-msFc (SEQ ID No. 4) cloning, the same protocol described above was followed, except that the pMB-SV5 vector contained the coding sequence of the mouse Fc domain (SEQ ID No. 31).

The nucleotide sequence of the expression vector coding for ICOS-msFc is set forth in SEQ ID No. 22.

To generate the human mutated $^{F119S}$ICOS-Fc construct (SEQ ID No. 6), the mutation F119S in the extracellular portion of human ICOS was introduced with a forward primer (5' TCAATTTTTGATC<u>CTCCTCC</u>TT<u>C</u>TAAAGTAACTCTTACAGG 3'-SEQ ID No.: 15, Sigma-Genosys) annealing at BseRI digestion site and ICOS human reverse NheI primer (5' <u>GCTAGC</u>AAGTTGTGATTCATAAATATGC 3'-SEQ ID No.: 14, Sigma-Genosys). The nucleotide sequence of the extracellular portion of human mutated $^{F119S}$ICOS is set forth in SEQ ID No. 26. The mutated fragments were cloned into the pMB-SV5 plasmid with the coding sequence of the human Fc domain, after digestion with BseRI (cod. R0581, New England Biolabs inc) and NheI enzymes.

The nucleotide sequence of the expression vector coding for $^{F119S}$ICOS-Fc is set forth in SEQ ID No. 23.

To generate the mouse ICOS fused with the human Fc (msICOS-huFc) construct (SEQ ID No. 24), the nucleotide sequence encoding the extracellular portion of mouse ICOS (SEQ ID No. 16) was amplified with specific primers: ICOS mouse forward BsshII primer (5' TTG<u>GCGCGC</u>ATGCCGAAATCAATGGCTCGGCCGATC 3'-SEQ ID No.: 17, Sigma-Genosys) and ICOS mouse reverse NheI primer (5' CTA<u>GCTAGC</u>TAGCCAGAGCTTCAGCTGGC 3'-SEQ ID No.: 18, Sigma-Genosys). The vector used in this cloning was the pMB-SV5 with the coding sequence of the mouse Fc domain.

The nucleotide sequence of the expression vector coding for msICOS-huFc is set forth in SEQ ID No. 25.

The plasmid DNA was transformed into One Shot® TOP10 Chemically Competent *Escherichia Coli* bacterial cells (*E. coli*; cod. C4040-03, Life Technologies, Carlsbad, Calif., USA). The resulting colonies were screened using specific primers: P-Hygro sense (5' CTGCTTACTGGCTTATCG 3'-SEQ ID No. 19, Sigma-Genosys) and P-Hygro antisense (5' CAGATGGCTGGCAACTAG 3'-SEQ ID No. 20, Sigma-Genosys) and the construct was confirmed by sequencing. Finally, the plasmid DNA was transfected using FreeStyle™ MAX Reagent (cod. 16447100, Life technologies) into Chinese Hamster Ovarian-suspension cell line (CHO-s) (cod. R8/00-07, Invitrogen). The stable clones were obtained thanks to the presence of Hygromycin resistance in the vector; to this end the clones were grown under selection with Hygromycin-B (cod. 10687-010, Invitrogen) at the concentration of 0.2 mg/ml that allow full selection of transfected cells. The cells were grown in serum free IMDM medium (cod. BE12-915F01, Lonza, Basel, Switzerland) and the serum free culture supernatants were purified using Protein G Sepharose™ 4 Fast Flow columns (cod. 17-0618-01, GE Healthcare, Piscataway Township, N.J., USA).

Immunofluorescence

The osteoclasts phenotype was assessed by immunofluorescence and flow cytometry (BD, Bioscience, San Diego, Calif., USA) using the appropriate FITC-, PE-, and APC-conjugated monoclonal antibodies (mAb) to CD14 (cod. 21270146, Immunotools, Friesoythe, Germany), Catepsin-K (cod. BS1611R-FITC, Bioss Inc., Woburn, Mass., USA), and B7h (cod.FAB165P, R&D Systems). Levels of Catepsin-K were evaluated after cell permeabilization using the FIX and PERM kit (cod. GAS003, Invitrogen) following the manufacturer's instructions.

Actin staining was performed on cells fixed on glass coverslip with 4% paraformaldehyde (cod. 76240, Sigma-Aldrich, Saint Louis, Mo., USA), washed and then permeabilized with a solution containing 5% FBS, 1% bovine serum albumin (BSA, cod. 05479-250G, Sigma-Aldrich) and 0.1% Triton X-100 (cod. T9284, Sigma-Aldrich) for 1 hrs at room temperature. Then, the coverslip were stained with FITC-conjugated phalloidin (cod. F432, Invitrogen) in a solution of 0.1% Triton X-100, 1% BSA, 2% FBS. After 2 hrs, cells were washed with PBS plus 0.1% Triton X-100 for 10 minutes and observed by a phase-contrast microscope Axiovert 40 CFL (Carl Zeiss, Oberkochen, Germany), photographed with a Retiga 200R digital camera (QImaging, Surrey, BC, Canada), and analyzed with the Image Pro Plus Software for micro-imaging (Media Cybernetics, version5.0, Bethesda, Md., USA).

Tartrate-Resistant Acid Phosphatase (TRAP) Assay

TRAP activity was assessed on cells fixed on glass coverslips with a commercial kit (cod. 387A-1KT, Sigma-Aldrich) composed of 25% Citrate Solution (citric acid 18 mmol/l, sodium citrate 9 mmol/l, sodium chloride 12 mmol/l, pH 3.6), 65% acetone and 10% formaldehyde at 37%, for about 30 seconds. Then, the coverslips were washed with deionized water, stained with Fast Garnet GBC Base Solution (7 mg/ml, Sigma-Aldrich), and observed by contrast phase microscopy. The TRAP positivity was analyzed with an imaging system (Image-Pro Plus).

Calcium Release Assay

Monocytes ($0.5 \times 10^6$) were plated on 24 well Osteo Assay Surface culture plates (cod. CLS3987, Corning Inc., Corning, N.Y., USA), and differentiated to MDOCs as described above adding the ICOS reagents at day 14. At day 21 of culture, cells were washed and incubated for other 24 hrs with fresh medium. Supernatants were then collected and the calcium level was evaluated by a calcium colorimetric assay Kit (cod. MAK022-1KT, Sigma-Aldrich).

In Vivo Analysis

Soluble RANKL (cod. GWB-P09451, GenWay Biotech. Inc, San Diego, Calif., USA; 1 mg/kg) was injected i.p. daily for 3 days into 7-week-old C57BL/6 female mice (cod. 057, Harlan Laboratories, Indianapolis, Ind., USA), as reported by Tomimori Y. et al.[7], alone or in combination with 100 µg of msICOS-huFc (a fusion protein containing the extracellular portion of the mouse ICOS (SEQ ID No. 28)) fused to the human IgG1 Fc (SEQ ID No. 3), or $^{F119S}$ICOS-Fc.

Control mice were injected with PBS or 100 µg ICOS-msFc, or $^{F119S}$ICOS-Fc but not with RANKL. The mice were sacrificed 4 hrs after the last injection, and blood samples, tibias, and femora were harvested for analysis. Mice were bred under pathogen-free conditions in the animal facility of the Department of Health Sciences and were treated in accordance with the University Ethical Committee.

Samples of the tibia and femora were fixed at room temperature for 2 days in Concentrated neutral buffered formalin diluted to 4% in PBS pH 6.9 (cod. F0033, Diapth, Martinengo, BG Italy) and dehydrated in ascending concentrations of ethanol (cod. 02860-2.5 L, Sigma-Aldrich) for one night before performing a three-step impregnation in methylmethacrylate (MMA) monomer (cod. 8005902500, Merck, Darmstadt, Germany) for at least 3 days. For embedding, specimen blocks were impregnated in 80% (vol/vol) stabilized MMA, 20% (vol/vol) Plastoid N (cod. 5866, Rohm Pharma, Germany) for 2 hrs in uncapped vials under vacuum and embedded in capped 10 mL glass vials (water bath, cod. BR778012, Sigma-Aldrich) at 37° C. overnight. After polymerization, the glass vials were removed and moistened sections (50 mm) were cut on a Leica SP 1600 Saw Microtome with a rotating diamond saw blade for high-quality sample preparation of hard materials for microscopical analysis and mounted on polyethylene slides. Cut was performed on the long axis of the bone and the sections were stained using light-green (cod. 1159410025, Merck) and basic fuchsine (cod. 47860, Sigma-Aldrich) for histological evaluation. The sections were then examined histomorphologically and morphometrically by an investigator blinded to the identity of the material. These measurements were performed using a light microscope and analyzed with Leica imaging software (DFC320 Leica digital camera and software Leica QWin Plusv2.6). All measurements were performed at a magnification of 20×. Cortical bone morphology included tissue volume, medullary volume (Me.v) and bone volume (Bv=tissue volume—Me.v). Endocortical and periosteal bone surface were also measured.

Western Blot

MDOCs at T21 were treated with either ICOS-Fc or ICOS-msFc or $^{F119S}$ICOS-Fc or two different anti-B7h antibodies: anti human B7h (cod. BMS16-5889-82, eBioscience, Inc. San Diego, Calif., USA; clone MIH12) and anti human B7h (cod. MAB1651, R&D Systems; clone 136716).

MDOCs were lysed in 50 mM Tris-HCl pH 7.4, 150 mM NaCl (cod. S7653 Sigma-Aldrcih), 5 mM EDTA (cod. E6758 Sigma Aldrich), 1% NP-40 (cod. Sigma-Aldrich) with phosphatase and protease inhibitor cocktails (cod. P2850 and cod. P8340, Sigma-Aldrich). Then, 30 µg of proteins were run on 10% SDS PAGE gels and transferred onto Hybond-C extra nitrocellulose membranes (cod. 10600016, Ge Healthcare, Piscataway, N.J., USA). The membranes were then probed with antibodies to phospho-p38-MAPK (cod. 9211, Cell Signaling Technology, Danvers, Mass., USA) and p38-MAPK (cod. 9212, Cell Signaling Technology), followed by anti-rabbit HRP-conjugated secondary antibody (cod. A0545, Sigma-Aldrich). The bands were detected via chemiluminescence using the VersaDoc Imaging System (Bio-Rad Laboratories, Hercules, Calif., USA) and densitometric analysis was performed with the Multi-Analyst software (version 1.1, Bio-Rad Laboratories).

Ovariectomy

Bilateral ovariectomy (OVX) was performed in 6/8-weeks-old female C57BL/6 mice anesthetized with a mix of Zoletil® (60 mg/kg) and Xilazina® (20 mg/kg) i.p. One day after surgery, mice were treated with seven i.p. injections (1 every 4 days for 4 weeks) of either PBS or msICOS-msFc (400 µg). They were sacrificed 4 days after the last injection and organs and bones were collected for analysis.

Data Analysis

Statistical analysis were performed using ANOVA with Dunnett's test. $p<0.05$ was considered significant. The statistical analysis were performed with GraphPad Instat software (GraphPad Software, San Diego, Calif., USA).

Results

B7h Expression in Osteoclasts

Monocyte-derived osteoclasts (MDOCs) were obtained by culturing CD14$^+$ monocytes for 21 days in differentiation medium containing M-CSF and RANKL. In order to assess the MDOCs differentiation and monitor B7h expression, the present inventors evaluated the cell morphology by optical microscopy and expression of surface CD14, marking monocytes, intracellular Cathepsin K, marking osteoclasts, and B7h, by three-color immunofluorescence and flow cytometry performed at the beginning (day 0, T0) and the end (day 21, T21) of the MDOCs differentiation culture and in the intermediate day 14 (T14) (FIG. 1).

Effects of B7h Triggering on Differentiating Osteoclasts

Since B7h is expressed during the MDOCs differentiation culture, the present inventors evaluated the effect of B7h triggering on differentiating MDOCs using ICOS-Fc. To assess the specificity of the ICOS effect, cells were also treated with either $^{F119S}$ICOS-Fc, that is a mutated form of ICOS incapable to bind B7h, or ICOS-msFc, in which the human ICOS is fused with a mouse Fcγ portion to minimize interaction with the human Fcγ receptors. Treatment of differentiating MDOCs was started at either T0 or T14 of the culture by adding the ICOS reagents to the differentiating medium. The culture was continued up to T21 to perform the $T^{0-21}$ and $T^{14-21}$ treatments.

Figure 2:
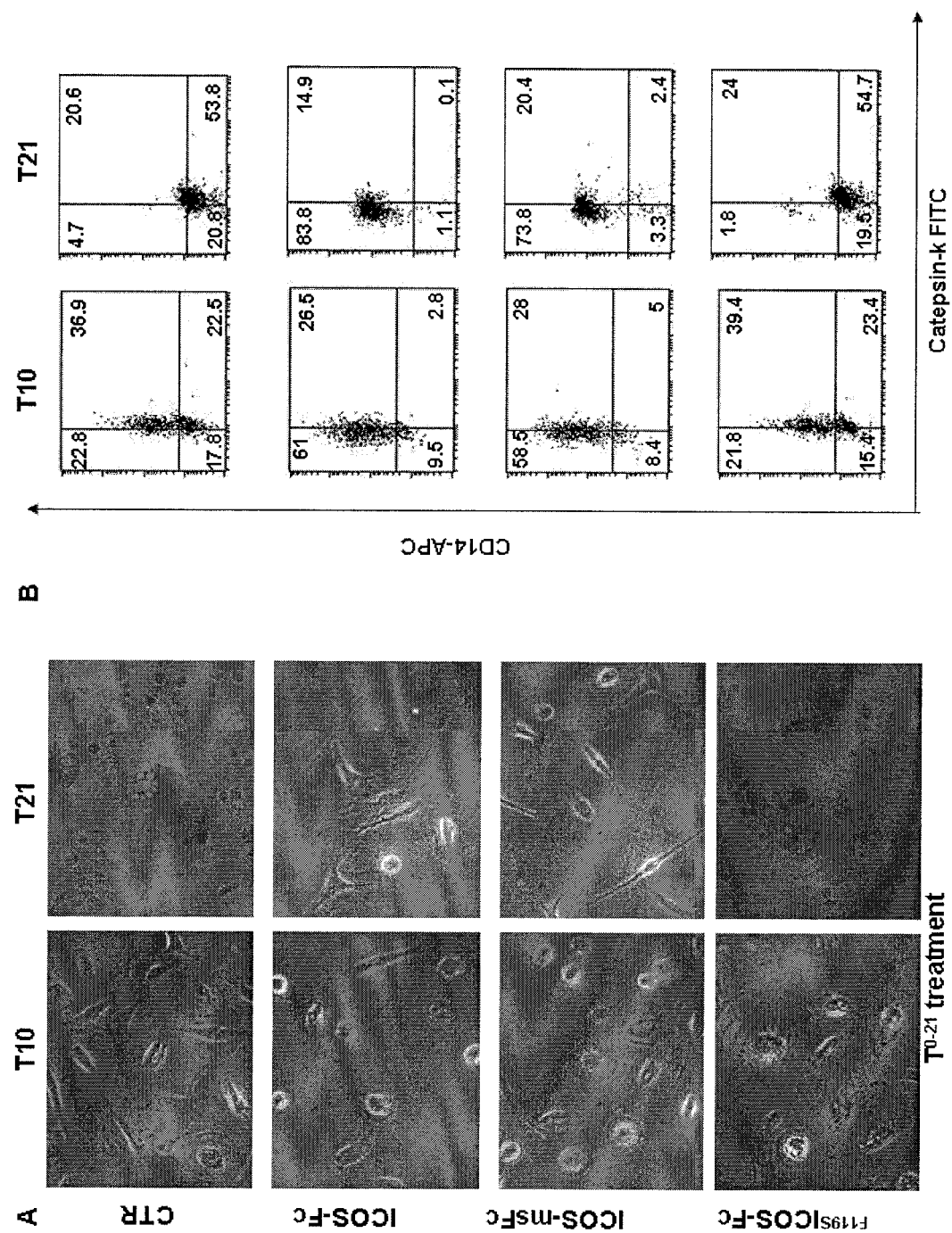
FIG. 2: Effect of ICOS-Fc on osteoclasts differentiation. Monocytes were induced to differentiate to MDOCs in the presence and absence of ICOS-Fc (1 µg/ml), ICOS-msFc (1 µg/ml), or $^{F119S}$ICOS-Fc (1 µg/ml) added at day 0 ($T^{0-21}$ treatment). A) Cells were photographed at T10 and T21 by phase-contrast microscopy. B) CD14 and Catepsin-K expression were assessed by flow cytometry in MDOCs at T10 and T21. Numbers in each panel indicate the % of positive cells vs the internal negative control. Panels are representative of 5 experiments.

Results showed that the $T^{0-21}$ treatment with ICOS-Fc or ICOS-msFc potently inhibited MDOCs differentiation. At day 10 (T10) cells displayed a round shape and at T21 they acquired a spindle-like morphology; moreover, they showed defective CD14 downregulation and catepsin K upregulation which mark osteoclast differentiation. By contrast, cells treated with $^{F119S}$ICOS-Fc did not display any difference from untreated cells showing the typical progression toward the MDOCs morphology and phenotype (FIG. 2).

Figure 3:
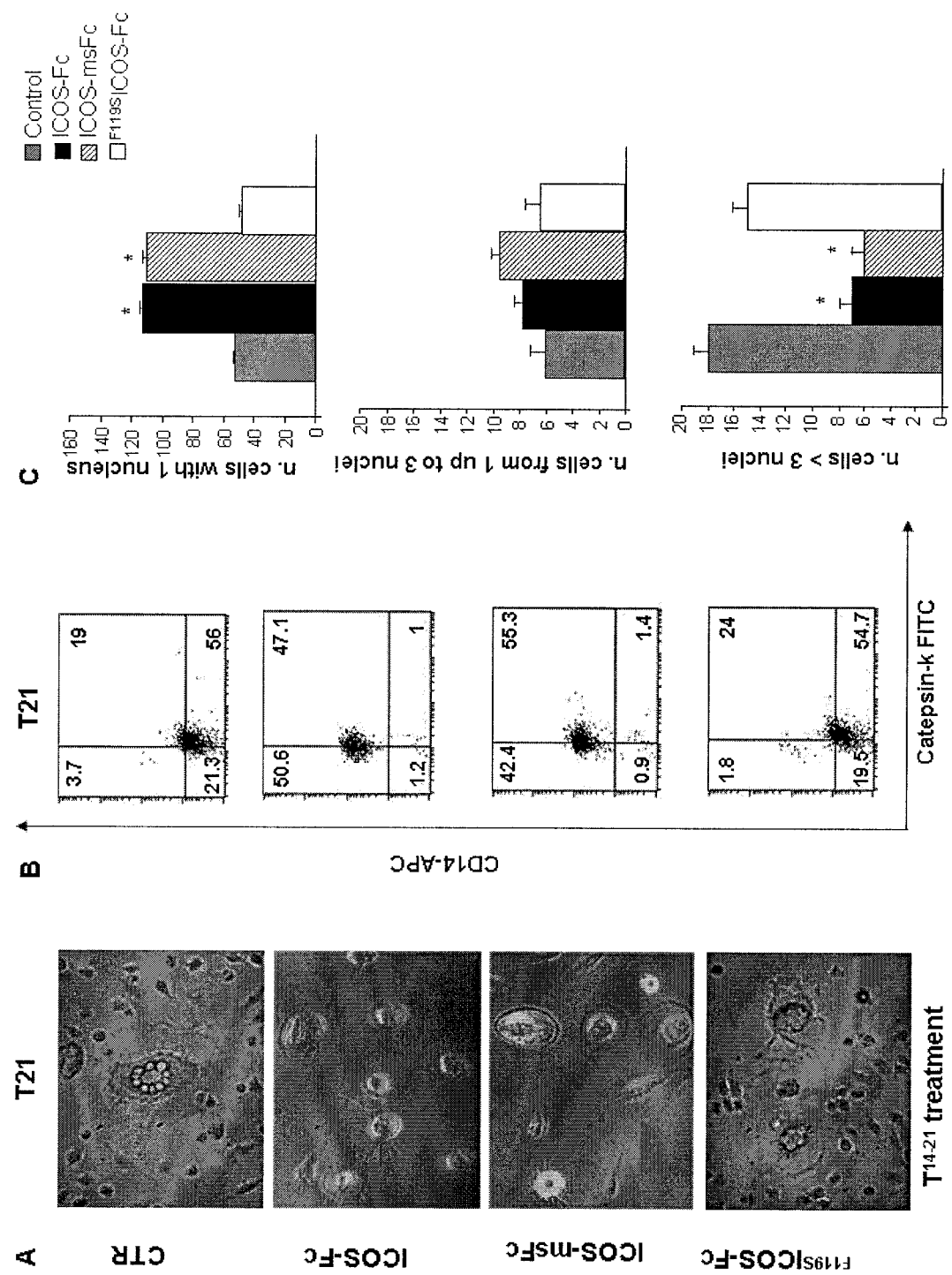
FIG. 3: Effect of ICOS-Fc on osteoclasts differentiation. Monocytes were induced to differentiate to MDOCs in the presence and absence of ICOS-Fc (1 µg/ml), ICOS-msFc (1 µg/ml), or $^{F119S}$ICOS-Fc (1 µg/ml) added from day 14 ($T^{14-21}$ treatment). A) Cells were photographed at T21 by phase-contrast microscopy. B) CD14 and Catepsin-K expression were assessed by flow cytometry in MDOCs at T21. Numbers in each panel indicate the % of positive cells vs the internal negative control. Panels are representative of 3 experiments. C) The bar graphs show the number of nuclei counted in each field at day 21 (mean from 5 fields); data are expressed as the mean±standard error of the mean (SEM) from 3 independent experiments (*: $p<0.01$ versus the control).

The $T^{14-21}$ treatment with either ICOS-Fc or ICOS-msFc showed a substantial slowing down of MDOCs differentiation since, at T21, cells displayed decreased cell size and nuclei pyknosis; decreased ability to adhere to the culture wells; increased number of cells with one nucleus only and decreased number of cells with >3 nuclei compared to untreated cells; and defective catepsin K upregulation and, especially, CD14 downregulation. Moreover, several cells displayed a star-like morphology that was not detected in untreated cells. By contrast, cells treated with $^{F119S}$ICOS-Fc were similar to untreated cells (FIG. 3).

Figure 4:
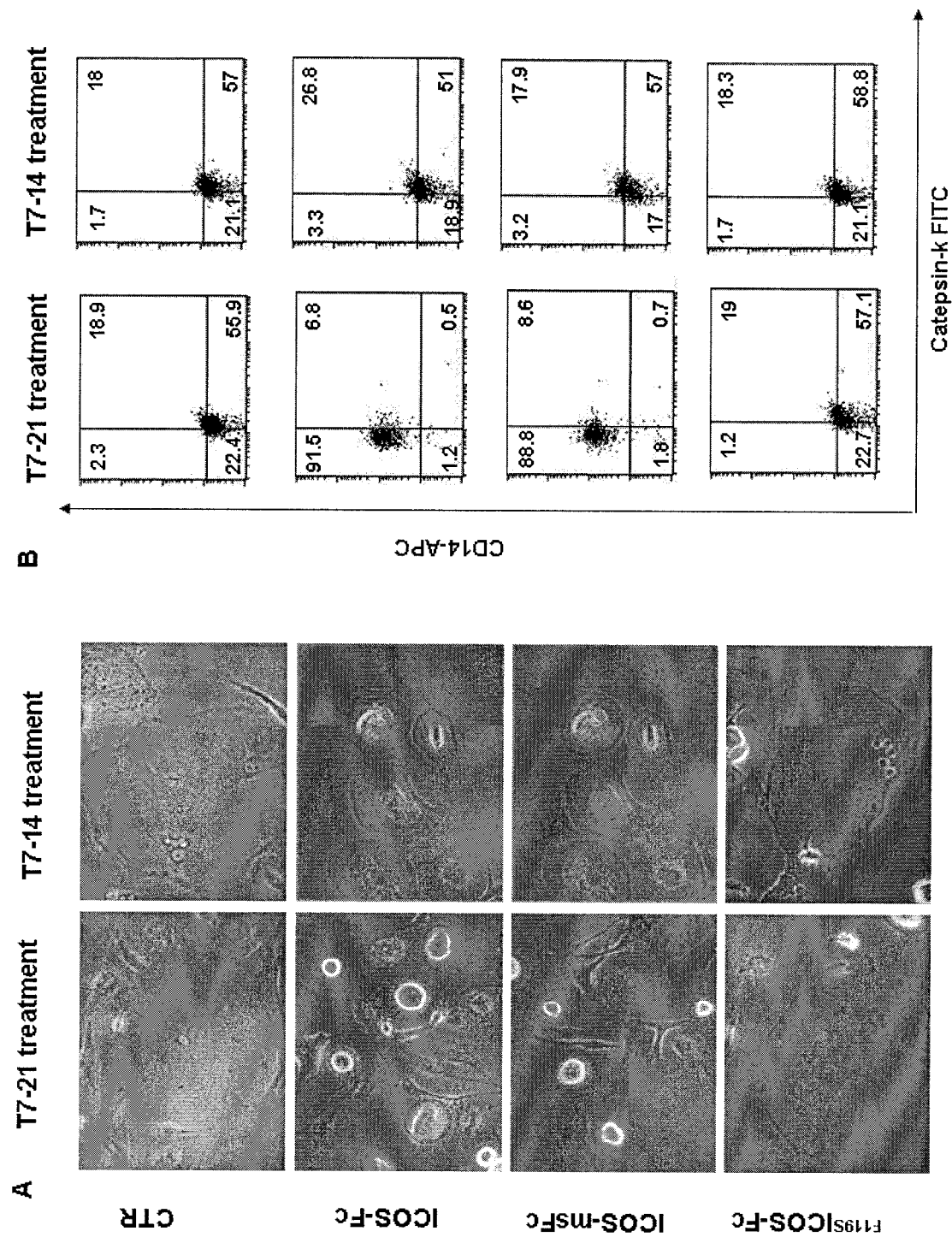
FIG. 4: Effect of ICOS-Fc on osteoclasts differentiation. Monocytes were induced to differentiate to MDOCs in the presence and absence of ICOS-Fc (1 µg/ml), ICOS-msFc (1 µg/ml) or $^{F119S}$ICOS-Fc (1 µg/ml) added from day 7 ($T^{7-21}$ and $T^{7-14}$ treatments). A) Cells were photographed at T21 by phase-contrast microscopy. B) CD14 and Catepsin-K expression were assessed by flow cytometry in MDOCs at T21. Numbers in each panel indicate the % of positive cells vs the internal negative control. Panels are representative of 3 experiments.

To assess reversibility of the ICOS-Fc effect, cells were treated with ICOS-Fc, ICOS-msFc, or $^{F119S}$ICOS-Fc at day 7 (T7) washed at T14 and then incubated to T21 in the presence ($T^{7-21}$ treatment) or absence ($T^{7-14}$ treatment) of ICOS-Fc, ICOS-msFc, or $^{F119S}$ICOS-Fc. Results showed that the $T^{7-21}$ treatment with ICOS-Fc or ICOS-msFc induced a morphology and phenotype similar to those described above for the $T^{14-21}$ treatment. The cells treated with $^{F119S}$ICOS-Fc did not display any difference from untreated cells. By contrast, the $T^{7-14}$ treatment induced a morphology and phenotype converging to that displayed by untreated cells (FIG. 4).

Effects of B7h Triggering on Differentiated Osteoclasts

Figure 5:
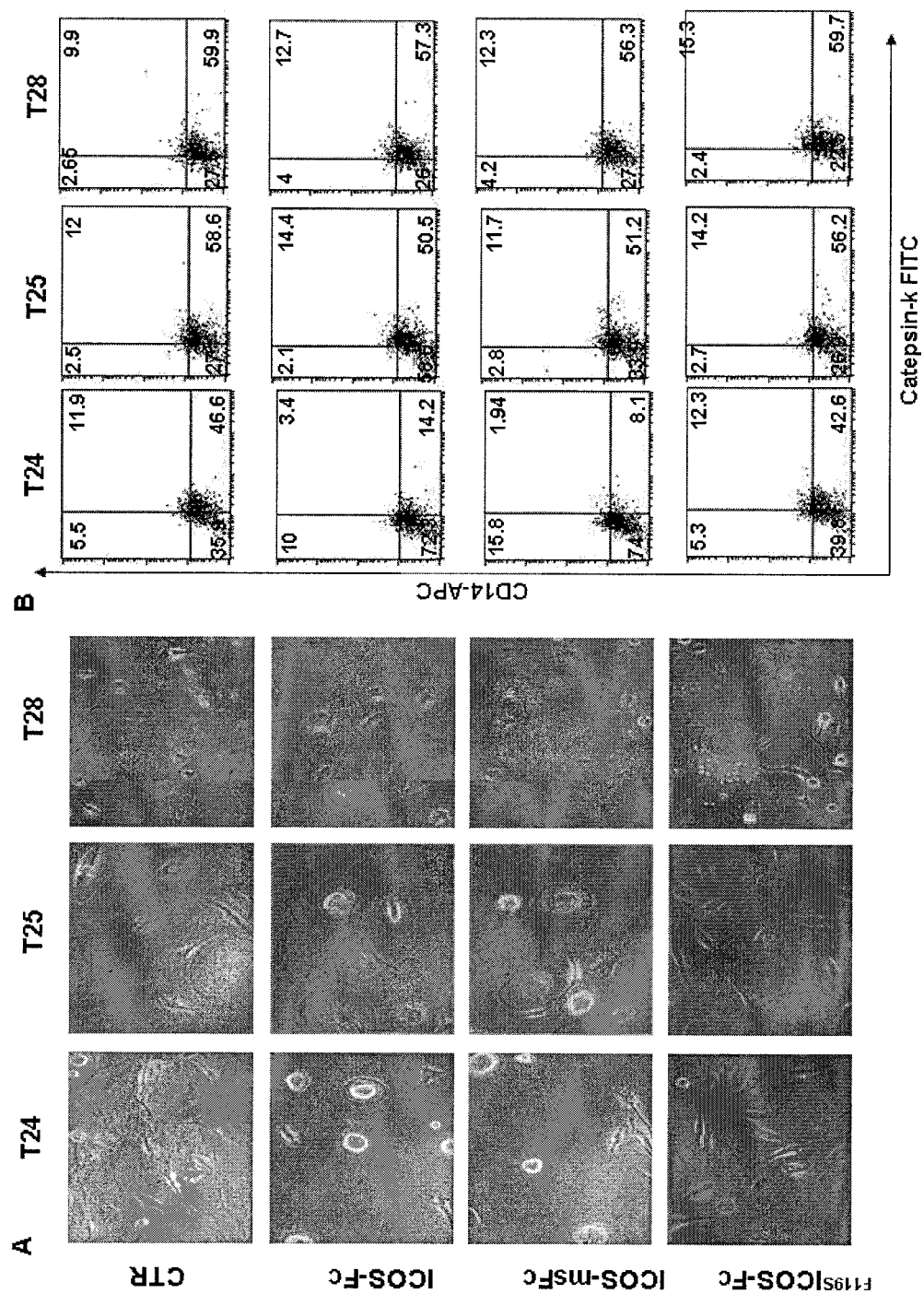
FIG. 5: Effect of ICOS-Fc on differentiated osteoclasts. After 21 days of differentiating culture, MDOCs were cultured in the presence and absence of ICOS-Fc (1 µg/ml), ICOS-msFc (1 µg/ml), or $^{F119S}$ICOS-Fc (1 µg/ml) for 3 other days ($T^{21-24}$ treatment), washed and then cultured for other 4 days (T25-T28). A) Cells were photographed at T24, T25 and, T28 by phase-contrast microscopy. B) CD14 and Catepsin-K expression were assessed by flow cytometry in MDOCs at T24, T25 and, T28. Numbers in each panel indicate the % of positive cells vs the internal negative control. Panels are representative of 3 experiments.

Treatment of already differentiated MDOCs was performed by treating cells at T21 with the ICOS reagents and analyzing them after 3 days (T24) to perform the $T^{21-24}$ treatment. Results showed that the $T^{21-24}$ treatment with ICOS-Fc or ICOS-msFc induced striking decrease of the cell and nuclei sizes, and decreased expression of catepsin K compared to untreated cells. Analysis of cell viability by the Trypan blue exclusion test showed that cells were viable. By contrast, the $T^{21-24}$ treatment with $^{F119S}$ICOS-Fc did not display any effect (FIG. 5).

To assess reversibility of the ICOS effect, $T^{21-24}$-treated cells were washed at T24 and incubated for 1 (T25) or 4 days (T28) in differentiation medium in the absence of ICOS-Fc. Results showed that cells treated with ICOS-Fc or ICOS-msFc and then grown in the absence of ICOS-Fc started to enlarge and upregulated catepsin K at T25, and displayed a MDOCs-like morphology, converging to that displayed by untreated cells, at T28 (FIG. 5). Analysis of cell viability by the Trypan blue exclusion test showed that cells were viable. By contrast, cells that had been untreated or treated with $^{F119S}$ICOS-Fc maintained their morphology and phenotype at T25 and T28.

Effect of B7h Triggering on Osteoclasts Function

Since the bone lytic activity of osteoclasts is related to their ability to secrete the content of intracytoplasmic granules containing several lytic enzymes including TRAP, the present inventors assessed the effect of the $T^{14-21}$ treatment with the ICOS reagents on TRAP expression assessed by a TRAP enzyme assay. Results showed that MDOCs treated with ICOS-Fc or ICOS-msFc display lower TRAP activity in terms of number of $TRAP^+$ cells and their staining intensity than untreated cells and cells treated with $^{F119S}$ICOS-Fc. This result was mostly evident in the cells with >3 nuclei (FIG. 6).

Since a key aspect of osteoclasts function is cytoskeleton organization to form the ruffle border at the erosion area delimited by the sealing zone, the present inventors analyzed the effect of the ICOS reagents on the cell actin organization by intracellular staining of $T^{14-21}$-treated MDOCs cells with FITC-phalloidin. Results showed that, in untreated MDOCs, actin was polarized with a pattern typical of the sealing zone delimiting the erosive lacuna of osteoclasts. By contrast, in cells treated with ICOS-Fc or ICOS-msFc, actin displayed a perinuclear distribution in a typical F-acting ring without signs of polarization. Cells treated with $^{F119S}$ICOS-Fc displayed a pattern similar to that of untreated cells (FIG. 7).

Figure 8:
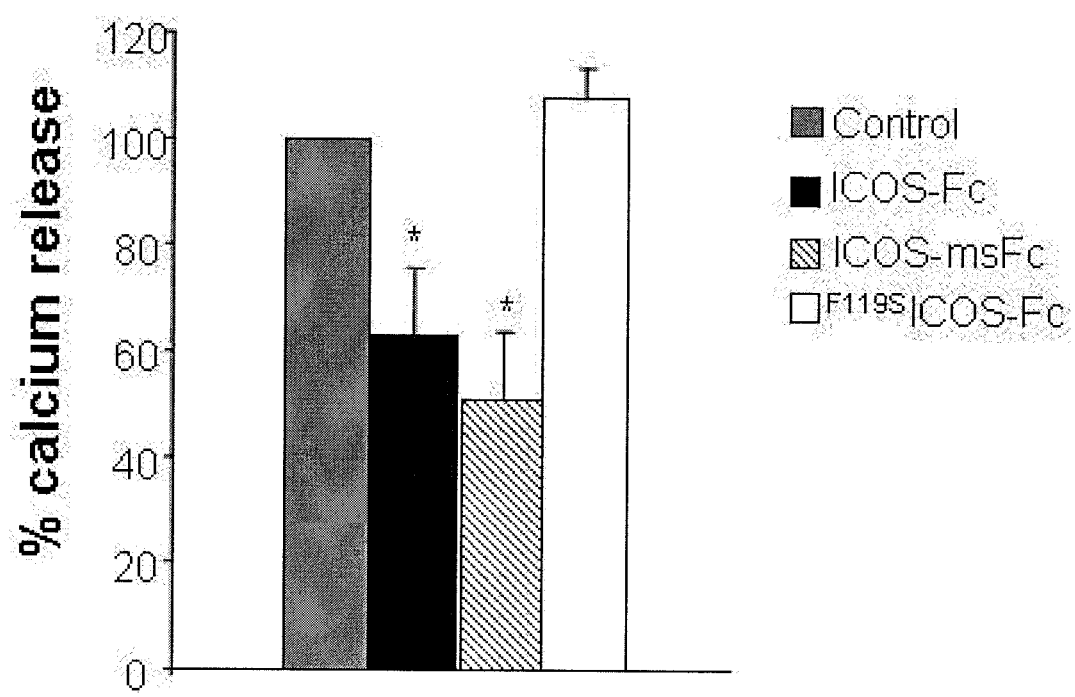
FIG. 8: Effect of B7h triggering on the osteoclasts osteolytic activity. Monocytes were plated on Osteo Surface plates and were induced to differentiate towards osteoclasts in the presence and absence of ICOS-Fc (1 µg/ml), ICOS-msFc (1 µg/ml), or $^{F119S}$ ICOS-Fc (1 µg/ml) as described in FIG. 2 ($T^{14-21}$ treatment). At Day 21, culture supernatants were harvested and examined for calcium release. Data represent the mean±SEM of the percentage of inhibition versus the control from 4 independent experiments performed in duplicate. (*: $p<0.05$ vs the control).

To assess the effect of ICOS on the osteolytic activity of MDOCs, the present inventors evaluated their ability to promote calcium release from crystalline calcium phosphate in vitro. MDOCs differentiation was induced in wells coated with a synthetic surface made of an inorganic crystalline calcium phosphate mimicking living bone material in the presence and absence of the ICOS reagents using a $T^{14-21}$ protocol. At T21, cells were washed and cultured for further 24 hrs in fresh medium, and release of calcium was then assessed in the culture supernatants using a colorimetric assay. Results showed that the $T^{14-21}$ treatment with ICOS-Fc or ICOS-msFc, significantly decreased the calcium release compared with untreated MDOCs, whereas $^{F119S}$ICOS-Fc did not display any effect (FIG. 8).

Figure 9:
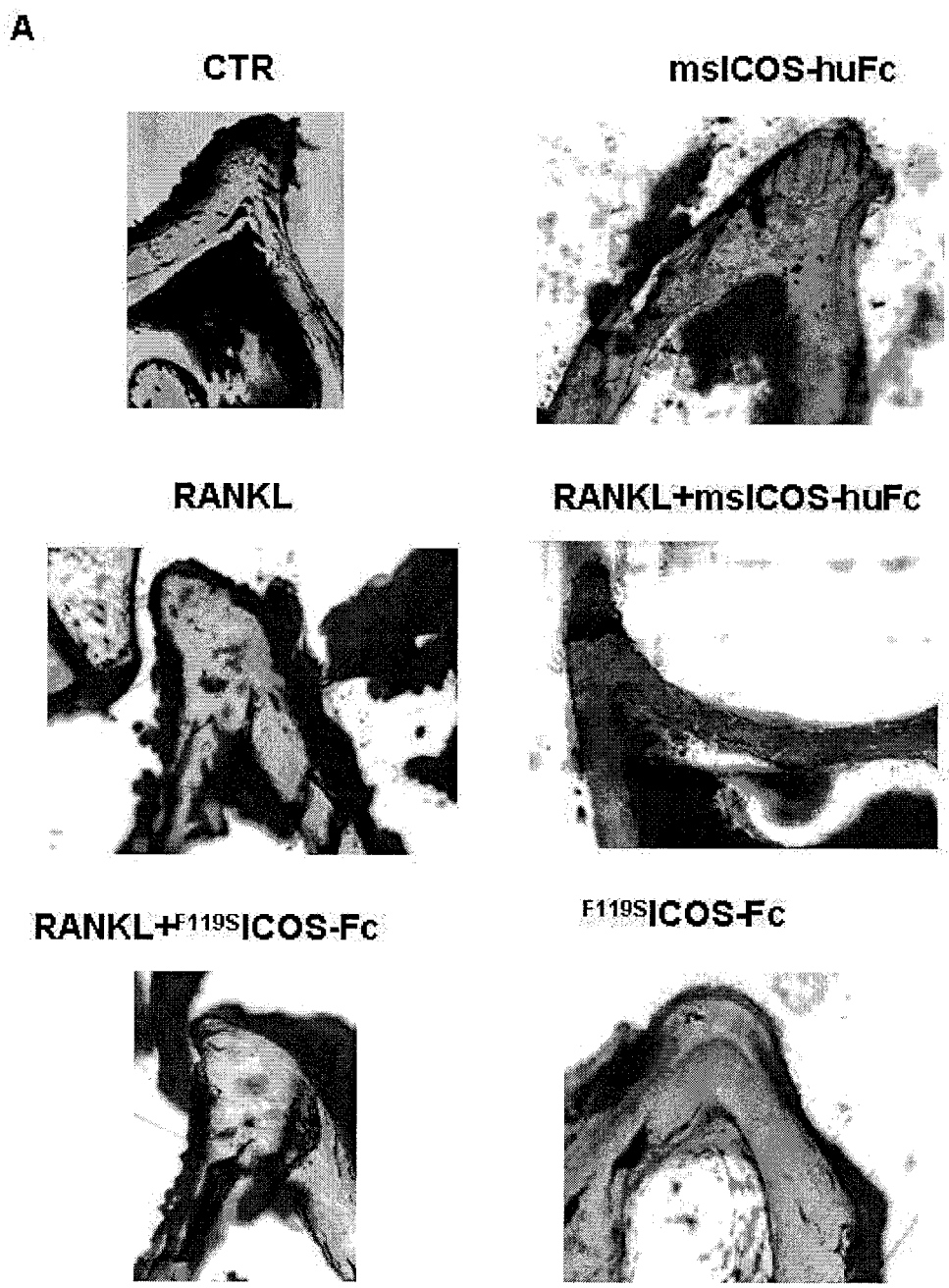
FIG. 9: Effects of treatment with ICOS-Fc in a mouse model of osteoporosis. Seven-week-old female C57BL/6 mice were injected with sRANKL 1 mg/Kg intra-peritoneally (i.p.) at 24-hours (hrs) intervals for 3 days together with either mouse ICOS-Fc (msICOS-huFc) (n=3) 100 µg/ml, or human $^{F119S}$ICOS-Fc (n=3) 100 µg/ml or phosphate buffered saline (PBS, control group, n=3). Mice were sacrificed 4 hrs after the last injection. A) Staining of undecalcified sections of tibia and femurs in the different-injected groups. B) Histogram showing the % mean±SEM of calcified bone in the cortical region (: $p<0.01$ or *: $p<0.001$ versus control mice receiving no treatments).

Finally, the present inventors assessed the effect of B7h triggering in vivo using a model of osteoporosis induced by treating mice with high doses of soluble RANKL. Female C57BL/6 mice (7-week-old) were injected i.p. daily for 3 days with RANKL (1 mg/kg) alone or in combination with either msICOS-huFc (formed by the mouse ICOS and human Fc) or $^{F119S}$ICOS-Fc (100 μg/mouse). The mice were sacrificed 4 hrs after the last injection. Histological analysis of tibias stained with Fuchsine and light green showed a marked bone loss in the RANKL-injected mice, which was significantly inhibited by co-treatment with msICOS-huFc but not with $^{F119S}$ICOS-Fc (FIG. 9).

Effects of B7h Triggering by Anti-B7h Antibodies on TRAP Staining

Figure 13:
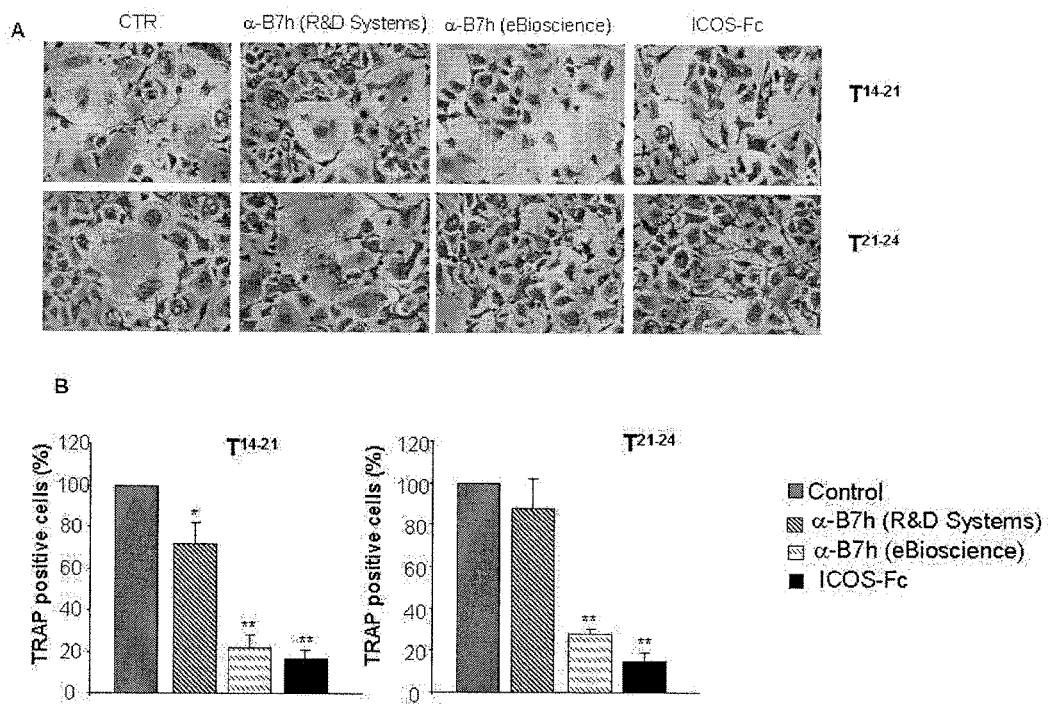
FIG. 13: Effect of anti-B7h antibodies on TRAP staining. MDOCs were treated with or without ICOS-Fc (1 µg/ml) or α-B7h/eBioscience (1 µg/ml) or α-B7h/R&D Systems (1 µg/ml) added at day 14 ($T^{14-21}$ treatment) or at day 21 ($T^{21-24}$ treatment). At day 21, the cell layer was stained with the Fast Garnet GBC Base Solution assessing TRAP activity. A) Microphotographs of the staining area were taken to assess TRAP positive cells. B) Data are expressed as mean±SEM of the percentage of the TRAP$^+$ cells from four different fields (*: $p<0.05$, **: $p<0.01$ versus the control).

The present inventors evaluated the effect of B7h triggering using two different anti-B7h antibodies (α-B7h/eBioscience and α-B7h/R&D Systems) on differentiating ($T^{14-21}$ treatment) and already mature ($T^{21-24}$ treatment) MDOCs, which were stained for TRAP. The $T^{14-21}$ treatment showed that untreated MDOCs appeared as giant cells with a dense TRAP staining. Treatment with α-B7h/eBioscience showed a substantial inhibition of MDOCs differentiation with decreased formation of multinuclear TRAP positive cells, comparable to the results obtained with ICOS-Fc. By contrast, treatment with α-B7h/R&D Systems displayed a minimal inhibitory effect. The $T^{21-24}$ treatment showed that untreated MDOCs appeared as giant cells with a dense TRAP staining. Treatment with α-B7h/eBioscience showed a substantial inhibition of MDOCs size and a decreased positivity of multinuclear TRAP positive cells comparable to the results obtained with ICOS-Fc. By contrast, treatment with α-B7h/R&D Systems displayed no inhibitory effect. The results are shown in FIG. 13.

Effect of B7h Triggering on MDOCs Signaling

Figure 14:
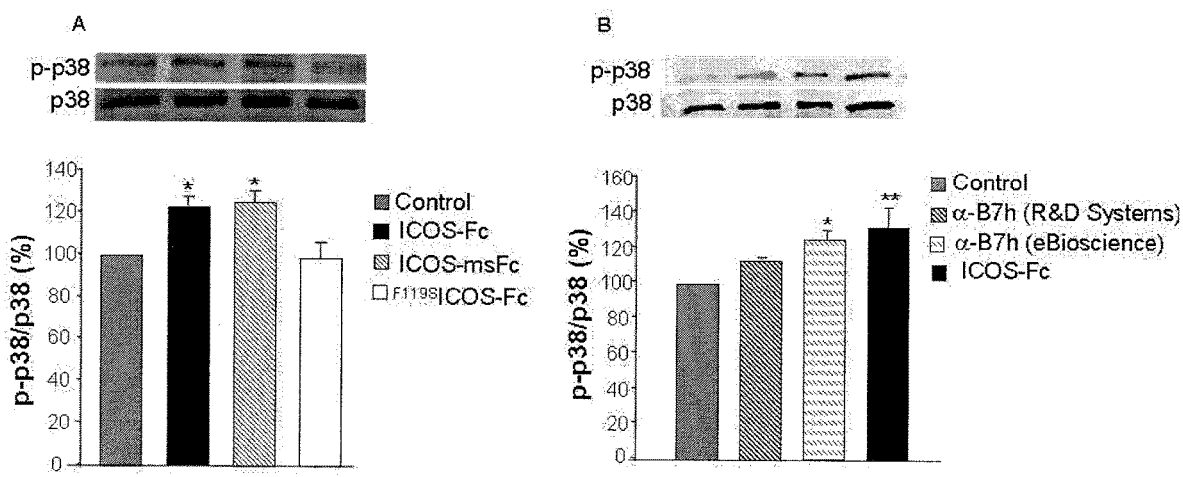
FIG. 14: Effect of ICOS reagents and anti-B7h antibodies on B7h signaling in MDOCs. Differentiated MDOCs were treated or not with A) either ICOS-Fc or ICOS-msFc or $^{F119S}$ICOS-Fc or B) α-B7h/eBioscience or α-B7h/R&D Systems antibodies (5 µg/ml) for 30 min at day 21. Then, expression of phospho-p38 was assessed by western blot. The same blots were also probed with anti-p38 antibody as a control. Data are expressed as the mean±SEM of the percentage of the phospho-p38 expression from 3 independent experiments (*: $p<0.05$ versus the control).

To investigate whether the inhibitory effect of B7h ligands on MDOCs differentiation and activity correlated with their agonistic activity on B7h, the present inventors assessed their effect on B7h signaling evaluated as induction of phosphorylation of p38 in MDOCs. MDOCs at T21 were treated in the absence and presence of either ICOS-Fc or ICOS-msFc or $^{F119S}$ICOS-Fc or α-B7h/eBioscience or α-B7h/R&D Systems (5 μg/ml) for 30 minutes, and the expression level of phospho-p38 MAPK was then assessed by western blot; expression of total p38 MAPK was assessed as a control. Results showed that, compared to untreated cells, phospho-p38 was upregulated by treatment with ICOS-Fc and ICOS-msFc but not with $^{F119S}$ICOS-Fc. The results obtained with the anti-B7h antibodies showed that phospho-p38 was upregulated by treatment with α-B7h/eBioscience, at a level comparable to that obtained with ICOS-Fc. By contrast, treatment with the α-B7h/R&D displayed a minimal effect. The results are shown in FIG. 14.

Effects of Treatment with ICOS-Fc in a Chronic Mouse Model of Osteoporosis

Figure 15:
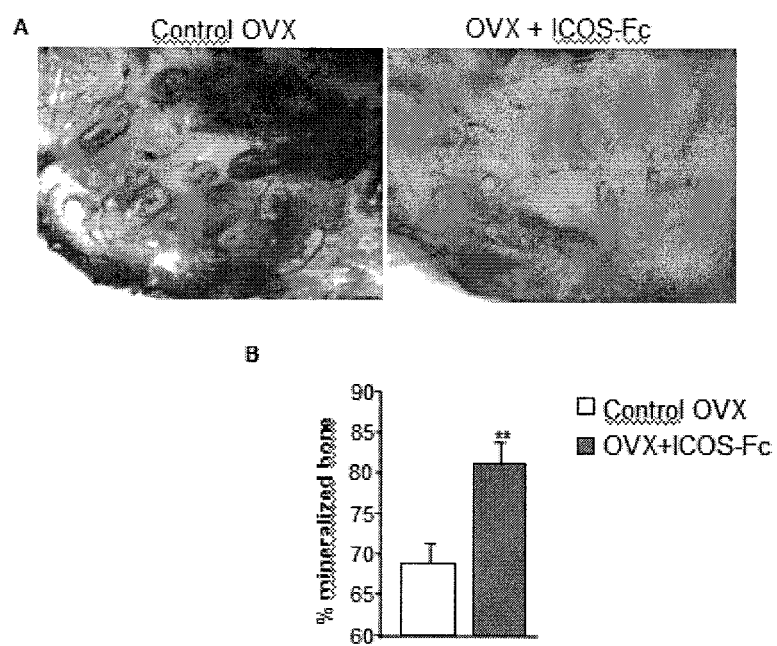
FIG. 15: Effects of treatment with ICOS-Fc in mouse osteoporosis induced by OVX. Mice were subjected to OVX and, 24 hours later, treated with ICOS-FC (msICOS-msFc) (n=3) or PBS (control group, n=3) for 4 weeks. A) Representative images of cortical bone from mice treated with PBS or ICOS-Fc. B) Bar graphs of proportion of calcified bone in the cortical region evaluated in 6 sections from each mouse (3 sections/leg). Data are expressed as mean±SEM (**: $p<0.01$ versus the control).

6/8-weeks-old female C57BL/6 mice received OVX and, after 24 hours, were injected i.p. every 4 days for 4 weeks with either PBS or a total mouse ICOS-Fc (formed by the mouse ICOS and the mouse Fc). The mice were sacrificed 4 days after the last injection. Morphometric measurements of mineralized bone tissue showed a marked bone loss in the PBS-injected mice and the bone loss was significantly inhibited by the treatment with ICOS-Fc. The results are shown in FIG. 15.

Naturally, while the principle of the invention remains the same, the details of construction and the embodiments may widely vary with respect to what has been described and illustrated purely by way of example, without departing from the scope of the present invention.

REFERENCES

1. Swallow et al. B7h, a novel costimulatory homolog of B7.1 and B7.2, is induced by TNF-α. *Immunity* 1999; 11:423-432.

2. Redoglia et al., Characterization of H4: a mouse T lymphocyte activation molecule functionally associated with the CD3/T cell receptor. *Eur J Immunol* 1996; 26:2781-9.
3. Buonfiglio et al. Characterization of a novel human surface molecule selectively expressed by mature thymocytes, activated T cells and subsets of T cell lymphomas. *Eur J Immunol.* 1999; 29:2863-74.
4. Hutloff et al. ICOS is an inducible T cell co-stimulator structurally and functionally related to CD28. *Nature* 1999; 397:263-266.
5. Buonfiglio et al. The T cell activation molecule H4 and the CD28-like molecule ICOS are identical. *Eur J Immunol* 2000; 30:3463-7.
6. Di Niro et al. Construction of miniantibodies for the in vivo study of human autoimmune diseases in animal models. *BMC Biotechnology* 2007; 7:46.
7. Tomimori et al. Evaluation of pharmaceuticals with a novel 50-hour animal model of bone loss. *J Bone Miner Res.* 2009; 24:1194-205.

The invention claimed is:

1. A method of treating osteoporosis or osteopenia, comprising the steps of: administering to a patient a medicament comprising an isolated ligand of receptor B7h, and thereby reducing osteoporosis or osteopenia in the patient, wherein the ligand comprises:
   a) a human ICOS polypeptide having the amino acid sequence set forth in SEQ ID NO: 29;
   b) a polypeptide having at least 90% sequence homology to the amino acid sequence set forth in SEQ ID NO: 29, wherein the polypeptide is capable of binding to receptor B7h;
   c) a fragment of a human ICOS polypeptide having the amino acid sequence set forth in SEQ ID NO: 29, wherein the fragment is capable of binding to receptor B7h;
   d) a human ICOS extracellular domain having the amino acid sequence set forth in SEQ ID NO: 2;
   e) a fragment of a human ICOS extracellular domain having the amino acid sequence set forth in SEQ ID NO: 2, wherein the fragment is capable of binding to receptor B7h; or
   f) a polypeptide having at least 90% sequence homology to the amino acid sequence set forth in SEQ ID NO: 2, wherein the polypeptide is capable of binding to receptor B7h, and
   wherein the patient
   has been diagnosed with osteopenia but has not been diagnosed with rheumatoid arthritis.

2. The method according to claim 1 wherein the ligand is to be administered by injection, or infusion.

3. The method according to claim 1 wherein the ligand is fused or conjugated to a stabilizing molecule.

4. The method according to claim 3 wherein the stabilizing molecule is selected from: polyethylene glycols or derivatives thereof, poly-L-lysine citramide, styrenemaleic acid anhydride, poly-hydroxypropylmetacrylamide, and human Fc antibody domain.

5. The method according to claim 4 wherein the polyethylene glycols derivatives are selected from: epoxide PEG, aldehyde PEG, nitrophenyl carbonate PEG, succinimidyl ester PEG, orthopyridyl disulfide PEGs, PEG-COOH activated with N-hydroxysuccinimide or hydroxybenzotriazole, PEG-polyacetal with pH-dependent hydrolysis, and PEG-dextrin.

6. The method according to claim 1 wherein the ligand is hyperglycosylated or conjugated to mannose residues.

7. The method according to claim 1 wherein the ligand of the receptor B7h has the ability of triggering the receptor B7h activity in osteoclasts thus inhibiting differentiation, maturation and/or function of osteoclasts.

8. The method according to claim 7 wherein the ligand is to be administered by injection, or infusion.

9. The method according to claim 7 wherein the ligand is fused or conjugated to a stabilizing molecule.

10. The method according to claim 7 wherein the ligand is hyperglycosylated or conjugated to mannose residues.

11. The method according to claim 10 wherein the stabilizing molecule is selected from: polyethylene glycols or derivatives thereof, poly-L-lysine citramide, styrenemaleic acid anhydride, poly-hydroxypropylmetacrylamide, and human Fc antibody domain.

12. The method according to claim 11 wherein the polyethylene glycols derivatives are selected from: epoxide PEG, aldehyde PEG, nitrophenyl carbonate PEG, succinimidyl ester PEG, orthopyridyl disulfide PEGs, PEG-COOH activated with N-hydroxysuccinimide or hydroxybenzotriazole, PEG-polyacetal with pH-dependent hydrolysis, and PEG-dextrin.

13. The method of claim 1, wherein the patient has cancer.

14. A method of treating osteoporosis or osteopenia, comprising the steps of: administering to a patient having osteoporosis or osteopenia a medicament comprising a ligand of receptor B7h, and thereby reducing osteoporosis or osteopenia in the patient, wherein the ligand comprises ICOS-Fc (SEQ ID NO: 1).

* * * * *

SEQUENCE LISTING

<160> NUMBER OF SEQ ID NOS: 31

<210> SEQ ID NO 1
<211> LENGTH: 380
<212> TYPE: PRT
<213> ORGANISM: artificial
<220> FEATURE:
<223> OTHER INFORMATION: ICOS-Fc

<400> SEQUENCE: 1

```
Met Gly Trp Ser Leu Ile Leu Leu Phe Leu Val Ala Val Ala Thr Gly
1               5                   10                  15

Gly Ala His Ala Glu Ile Asn Gly Ser Ala Asn Tyr Glu Met Phe Ile
                20                  25                  30

Phe His Asn Gly Gly Val Gln Ile Leu Cys Lys Tyr Pro Asp Ile Val
            35                  40                  45

Gln Gln Phe Lys Met Gln Leu Leu Lys Gly Gly Gln Ile Leu Cys Asp
        50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Ala Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285
```

```
Phe Tyr Pro Ser Asp Ile Ala Val Glu Trp Glu Ser Asn Gly Gln Pro
    290                 295                 300
Glu Asn Asn Tyr Lys Thr Thr Pro Pro Val Leu Asp Ser Asp Gly Ser
305                 310                 315                 320
Phe Phe Leu Tyr Ser Lys Leu Thr Val Asp Lys Ser Arg Trp Gln Gln
                325                 330                 335
Gly Asn Val Phe Ser Cys Ser Val Met His Glu Ala Leu His Asn His
                340                 345                 350
Tyr Thr Gln Lys Ser Leu Ser Leu Ser Pro Gly Lys Thr Ser Gly Lys
                355                 360                 365
Pro Ile Pro Asn Pro Leu Leu Gly Leu Asp Ser Thr
    370                 375                 380

<210> SEQ ID NO 2
<211> LENGTH: 115
<212> TYPE: PRT
<213> ORGANISM: homo sapiens

<400> SEQUENCE: 2

Glu Ile Asn Gly Ser Ala Asn Tyr Glu Met Phe Ile Phe His Asn Gly
1               5                   10                  15
Gly Val Gln Ile Leu Cys Lys Tyr Pro Asp Ile Val Gln Gln Phe Lys
                20                  25                  30
Met Gln Leu Leu Lys Gly Gly Gln Ile Leu Cys Asp Leu Thr Lys Thr
            35                  40                  45
Lys Gly Ser Gly Asn Thr Val Ser Ile Lys Ser Leu Lys Phe Cys His
50                  55                  60
Ser Gln Leu Ser Asn Asn Ser Val Ser Phe Phe Leu Tyr Asn Leu Asp
65                  70                  75                  80
His Ser His Ala Asn Tyr Tyr Phe Cys Asn Leu Ser Ile Phe Asp Pro
                85                  90                  95
Pro Pro Phe Lys Val Thr Leu Thr Gly Gly Tyr Leu His Ile Tyr Glu
                100                 105                 110
Ser Gln Leu
        115

<210> SEQ ID NO 3
<211> LENGTH: 227
<212> TYPE: PRT
<213> ORGANISM: homo sapiens

<400> SEQUENCE: 3

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                35                  40                  45
Glu Asp Pro Glu Val Lys Phe Asn Trp Tyr Val Asp Gly Val Glu Val
            50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 4
<211> LENGTH: 375
<212> TYPE: PRT
<213> ORGANISM: artificial
<220> FEATURE:
<223> OTHER INFORMATION: ICOS-msFC

<400> SEQUENCE: 4

Met Gly Trp Ser Leu Ile Leu Leu Phe Leu Val Ala Val Ala Thr Gly
1               5                   10                  15

Gly Ala His Ala Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Ala Ser Gly Cys Lys Pro Cys Ile Cys
    130                 135                 140

Thr Val Pro Glu Val Ser Ser Val Phe Ile Phe Pro Pro Lys Pro Lys
145                 150                 155                 160

Asp Val Leu Thr Ile Thr Leu Thr Pro Lys Val Thr Cys Val Val Val
                165                 170                 175

Asp Ile Ser Lys Asp Asp Pro Glu Val Gln Phe Ser Trp Phe Val Asp
            180                 185                 190

Asp Val Glu Val His Thr Ala Gln Thr Lys Pro Arg Glu Glu Gln Ile
        195                 200                 205

Asn Ser Thr Phe Arg Ser Val Ser Glu Leu Pro Ile Met His Gln Asp
    210                 215                 220

Trp Leu Asn Gly Lys Glu Phe Lys Cys Arg Val Asn Ser Ala Ala Phe
225                 230                 235                 240
```

```
Pro Ala Pro Ile Glu Lys Thr Ile Ser Lys Thr Lys Gly Arg Pro Lys
            245                 250                 255

Ala Pro Gln Val Tyr Thr Ile Pro Pro Lys Glu Gln Met Ala Lys
        260                 265                 270

Asp Lys Val Ser Leu Thr Cys Met Ile Thr Asn Phe Phe Pro Glu Asp
            275                 280                 285

Ile Thr Val Glu Trp Gln Trp Asn Gly Gln Pro Ala Glu Asn Tyr Lys
        290                 295                 300

Asn Thr Gln Pro Ile Met Asp Thr Asp Gly Ser Tyr Phe Val Tyr Ser
305                 310                 315                 320

Lys Leu Asn Val Gln Lys Ser Asn Trp Glu Ala Gly Asn Thr Phe Thr
                325                 330                 335

Cys Ser Val Leu His Glu Gly Leu His Asn His His Thr Glu Lys Ser
            340                 345                 350

Leu Ser His Ser Pro Gly Lys Thr Ser Gly Lys Pro Ile Pro Asn Pro
        355                 360                 365

Leu Leu Gly Leu Asp Ser Thr
370                 375

<210> SEQ ID NO 5
<211> LENGTH: 222
<212> TYPE: PRT
<213> ORGANISM: mus musculus

<400> SEQUENCE: 5

Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
            20                  25                  30

Lys Val Thr Cys Val Val Val Asp Ile Ser Lys Asp Asp Pro Glu Val
        35                  40                  45

Gln Phe Ser Trp Phe Val Asp Asp Val Glu Val His Thr Ala Gln Thr
    50                  55                  60

Lys Pro Arg Glu Glu Gln Ile Asn Ser Thr Phe Arg Ser Val Ser Glu
65                  70                  75                  80

Leu Pro Ile Met His Gln Asp Trp Leu Asn Gly Lys Glu Phe Lys Cys
                85                  90                  95

Arg Val Asn Ser Ala Ala Phe Pro Ala Pro Ile Glu Lys Thr Ile Ser
            100                 105                 110

Lys Thr Lys Gly Arg Pro Lys Ala Pro Gln Val Tyr Thr Ile Pro Pro
        115                 120                 125

Pro Lys Glu Gln Met Ala Lys Asp Lys Val Ser Leu Thr Cys Met Ile
    130                 135                 140

Thr Asn Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
            180                 185                 190

Glu Ala Gly Asn Thr Phe Thr Cys Ser Val Leu His Glu Gly Leu His
        195                 200                 205

Asn His His Thr Glu Lys Ser Leu Ser His Ser Pro Gly Lys
    210                 215                 220
```

```
<210> SEQ ID NO 6
<211> LENGTH: 380
<212> TYPE: PRT
<213> ORGANISM: artificial
<220> FEATURE:
<223> OTHER INFORMATION: F119S - ICOS-Fc

<400> SEQUENCE: 6

Met Gly Trp Ser Leu Ile Leu Leu Phe Leu Val Ala Val Ala Thr Gly
1               5                   10                  15

Gly Ala His Ala Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Ser Lys Val Thr Leu Thr Gly Gly Tyr Leu
        115                 120                 125

His Ile Tyr Glu Ser Gln Leu Ala Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys Thr Ser Gly Lys
        355                 360                 365

Pro Ile Pro Asn Pro Leu Leu Gly Leu Asp Ser Thr
```

<210> SEQ ID NO 7
<211> LENGTH: 115
<212> TYPE: PRT
<213> ORGANISM: artificial
<220> FEATURE:
<223> OTHER INFORMATION: F119S mutated ICOS

<400> SEQUENCE: 7

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Ser Lys Val Thr Leu Thr Gly Gly Tyr Leu His Ile Tyr Glu
            100                 105                 110

Ser Gln Leu
        115
```

<210> SEQ ID NO 8
<211> LENGTH: 8
<212> TYPE: DNA
<213> ORGANISM: artificial
<220> FEATURE:
<223> OTHER INFORMATION: Kozak sequence

<400> SEQUENCE: 8 ccacatgg                                                                      8

<210> SEQ ID NO 9
<211> LENGTH: 41
<212> TYPE: DNA
<213> ORGANISM: artificial
<220> FEATURE:
<223> OTHER INFORMATION: secretory leader sequence

<400> SEQUENCE: 9
gctggagcct gatcctcctg ttcctcgtcg ctgtggctac a                                 41

<210> SEQ ID NO 10
<211> LENGTH: 82
<212> TYPE: DNA
<213> ORGANISM: artificial
<220> FEATURE:
<223> OTHER INFORMATION: mini intron sequence

<400> SEQUENCE: 10
gtaaggggct cacagtagca ggcttgaggt ctggacatat atatgggtga caatgacatc             60
cactttgcct ttctctccac ag                                                     82

<210> SEQ ID NO 11
<211> LENGTH: 42
<212> TYPE: DNA
<213> ORGANISM: artificial

```
<220> FEATURE:
<223> OTHER INFORMATION: SV5 tag

<400> SEQUENCE: 11
ggcaaaccaa tcccaaaccc actgctgggc ctggatagta ct                42

<210> SEQ ID NO 12
<211> LENGTH: 345
<212> TYPE: DNA
<213> ORGANISM: homo sapiens

<400> SEQUENCE: 12
gaaatcaatg gttctgccaa ttatgagatg tttatatttc acaacggagg tgtacaaatt    60
ttatgcaaat atcctgacat tgtccagcaa tttaaaatgc agttgctgaa agggggcaa    120 atactctgcg atctcactaa gacaaaagga agtggaaaca cagtgtccat taagagtctg   180
aaattctgcc attctcagtt atccaacaac agtgtctctt tttttctata caacttggac   240
cattctcatg ccaactatta cttctgcaac ctatcaattt ttgatcctcc tccttttaaa   300
gtaactctta caggaggata tttgcatatt tatgaatcac aactt                   345

<210> SEQ ID NO 13
<211> LENGTH: 30
<212> TYPE: DNA
<213> ORGANISM: artificial
<220> FEATURE:
<223> OTHER INFORMATION: ICOS forward BsshII primer

<400> SEQUENCE: 13
ggcgcgcatg ccgaaatcaa tggttctgcc                              30

<210> SEQ ID NO 14
<211> LENGTH: 28
<212> TYPE: DNA
<213> ORGANISM: artificial
<220> FEATURE:
<223> OTHER INFORMATION: ICOS reverse NheI primer

<400> SEQUENCE: 14
gctagcaagt tgtgattcat aaatatgc                                28

<210> SEQ ID NO 15
<211> LENGTH: 41
<212> TYPE: DNA
<213> ORGANISM: artificial
<220> FEATURE:
<223> OTHER INFORMATION: mutation F119S - forward primer

<400> SEQUENCE: 15 tcaattttg atcctcctcc ttctaaagta actcttacag g                  41

<210> SEQ ID NO 16
<211> LENGTH: 375
<212> TYPE: DNA
<213> ORGANISM: mus musculus

<400> SEQUENCE: 16
gaaatcaatg gctcggccga tcataggatg ttttcatttc acaatggagg tgtacagatt    60
tcttgtaaat accctgagac tgtccagcag ttaaaaatgc gattgttcag agagagagaa   120
gtcctctgcg aactcaccaa gaccaaggga agcggaaatg cggtgtccat caagaatcca   180
atgctctgtc tatatcatct gtcaaacaac agcgtctctt ttttcctaaa caacccagac   240
```

| | |
|---|---|
| agctcccagg gaagctatta cttctgcagc ctgtccattt ttgacccacc tccttttcaa | 300 |
| gaaaggaacc ttagtggagg atatttgcat atttatgaat cccagctctg ctgctgccag | 360 |
| ctgaagctct ggcta | 375 |

<210> SEQ ID NO 17
<211> LENGTH: 36
<212> TYPE: DNA
<213> ORGANISM: artificial
<220> FEATURE:
<223> OTHER INFORMATION: ICOS mouse forward BsshII primer

<400> SEQUENCE: 17

| | |
|---|---|
| ttggcgcgca tgccgaaatc aatggctcgg ccgatc | 36 |

<210> SEQ ID NO 18
<211> LENGTH: 29
<212> TYPE: DNA
<213> ORGANISM: artificial
<220> FEATURE:
<223> OTHER INFORMATION: ICOS mouse reverse NheI primer

<400> SEQUENCE: 18

| | |
|---|---|
| ctagctagct agccagagct tcagctggc | 29 |

<210> SEQ ID NO 19
<211> LENGTH: 18
<212> TYPE: DNA
<213> ORGANISM: artificial
<220> FEATURE:
<223> OTHER INFORMATION: P-Hygro sense primer

<400> SEQUENCE: 19

| | |
|---|---|
| ctgcttactg gcttatcg | 18 |

<210> SEQ ID NO 20
<211> LENGTH: 18
<212> TYPE: DNA
<213> ORGANISM: artificial
<220> FEATURE:
<223> OTHER INFORMATION: P-Hygro antisense primer

<400> SEQUENCE: 20

| | |
|---|---|
| cagatggctg gcaactag | 18 |

<210> SEQ ID NO 21
<211> LENGTH: 6729
<212> TYPE: DNA
<213> ORGANISM: artificial
<220> FEATURE:
<223> OTHER INFORMATION: expression vector for ICOS-Fc

<400> SEQUENCE: 21

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctgtctaga    900
tgccaccatg ggctggagcc tgatcctcct gttcctcgtc gctgtggcta caggtaaggg    960
gctcacagta gcaggcttga ggtctggaca tatatgggg tgacaatgac atccactttg    1020
cctttctctc cacaggtggc gcgcatgccg aaatcaatgg ttctgccaat tatgagatgt   1080
ttatatttca aacggaggt gtacaaattt tatgcaaata tcctgacatt gtccagcaat    1140
ttaaaatgca gttgctgaaa gggggcaaa tactctgcga tctcactaag acaaaaggaa    1200
gtggaaacac agtgtccatt aagagtctga aattctgcca ttctcagtta ccaacaaca    1260 gtgtctcttt ttttctatac aacttggacc attctcatgc caactattac ttctgcaacc   1320
tatcaatttt tgatcctcct cctttaaag taactcttac aggaggatat ttgcatattt    1380
atgaatcaca acttgctagc gacaaaactc acacatgccc accgtgccca gcacctgaac   1440
tcctgggggg accgtcagtc ttcctcttcc ccccaaaacc caaggacacc ctcatgatct   1500
cccggacccc tgaggtcaca tgcgtggtgg tggacgtgag ccacgaagac cctgaggtca   1560
agttcaactg gtacgtggac ggcgtggagg tgcataatgc caagacaaag ccgcgggagg   1620
agcagtacaa cagcacgtac cgtgtggtca gcgtcctcac cgtcctgcac caggactggc   1680
tgaatggcaa ggagtacaag tgcaaggtct ccaacaaagc cctcccagcc cccatcgaga   1740
aaaccatctc caaagccaaa gggcagcccc gagaaccaca ggtgtacacc ctgcccccat   1800
cccgggagga tgaccaag aaccaggtca gcctgacctg cctggtcaaa ggcttctatc     1860
ccagcgacat cgccgtggag tgggagagca atgggcagcc ggagaacaac tacaagacca   1920
cgcctcccgt gctggactcc gacggctcct tcttcctcta tagcaagctc accgtggaca   1980
agagcaggtg gcagcagggg aacgtcttct catgctccgt gatgcatgag gctctgcaca   2040
accactacac gcagaagagc ctctccctgt ccccgggtaa aactagtggc aaaccaatcc   2100
caaacccact gctgggcctg gatagtactt aaaagcttaa acccgctgat cagcctcgac   2160
tgtgccttct agttgccagc catctgttgt ttgcccctcc cccgtgcctt ccttgaccct   2220
ggaaggtgcc actcccactg tccttttccta ataaaatgag gaaattgcat cgcattgtct   2280
gagtaggtgt cattctattc tggggggtgg ggtggggcag gacagcaagg gggaggattg   2340
ggaagacaat agcaggcatg ctggggatgc ggtgggctct atggcttctg aggcggaaag   2400
aaccagctgg ggctctaggg ggtatcccca cgcgccctgt agcggcgcat taagcgcggc   2460
gggtgtggtg gttacgcgca gcgtgaccgc tacacttgcc agcgccctag cgcccgctcc   2520
tttcgctttc ttcccttcct ttctcgccac gttcgccggc tttccccgtc aagctctaaa   2580
tcgggggctc cctttagggt tccgatttag tgctttacgg cacctcgacc ccaaaaaact   2640
tgattagggt gatggttcac gtagtgggcc atcgccctga tagacggttt ttcgcccttt   2700
gacgttggag tccacgttct ttaatagtgg actcttgttc caaactggaa caacactcaa   2760
ccctatctcg gtctattctt ttgatttata agggattttg ccgatttcgg cctattggtt   2820
```

```
aaaaaatgag ctgatttaac aaaaatttaa cgcgaattaa ttctgtggaa tgtgtgtcag    2880
ttagggtgtg gaaagtcccc aggctcccca gcaggcagaa gtatgcaaag catgcatctc    2940
aattagtcag caaccaggtg tggaaagtcc ccaggctccc cagcaggcag aagtatgcaa    3000
agcatgcatc tcaattagtc agcaaccata gtcccgcccc taactccgcc catcccgccc    3060
ctaactccgc ccagttccgc ccattctccg ccccatggct gactaatttt ttttatttat    3120
gcagaggccg aggccgcctc tgcctctgag ctattccaga agtagtgagg aggctttttt    3180
ggaggcctag gcttttgcaa aaagctcccg ggagcttgta tatccatttt cggatctgat    3240
cagcacgtga tgaaaaagcc tgaactcacc gcgacgtctg tcgagaagtt tctgatcgaa    3300
aagttcgaca gcgtctccga cctgatgcag ctctcggagg gcgaagaatc tcgtgctttc    3360
agcttcgatg taggagggcg tggatatgtc ctgcgggtaa atagctgcgc cgatggtttc    3420
tacaaagatc gttatgttta tcggcacttt gcatcggccg cgctcccgat tccggaagtg    3480
cttgacattg ggaattcag cgagagcctg acctattgca tctcccgccg tgcacagggt    3540
gtcacgttgc aagacctgcc tgaaaccgaa ctgcccgctg ttctgcagcc ggtcgcggag    3600
gccatggatg cgatcgctgc ggccgatctt agccagacga gcgggttcgg cccattcgga    3660
ccgcaaggaa tcggtcaata cactacatgg cgtgatttca tatgcgcgat gctgatcccc    3720
catgtgtatc actggcaaac tgtgatggac gacaccgtca gtgcgtccgt cgcgcaggct    3780
ctcgatgagc tgatgctttg ggccgaggac tgccccgaag tccggcacct cgtgcacgcg    3840
gatttcggct ccaacaatgt cctgacggac aatggccgca taacagcggt cattgactgg    3900
agcgaggcga tgttcgggga ttcccaatac gaggtcgcca acatcttctt ctggaggccg    3960
tggttggctt gtatggagca gcagacgcgc tacttcgagc ggaggcatcc ggagcttgca    4020
ggatcgccgc ggctccgggc gtatatgctc cgcattggtc ttgaccaact ctatcagagc    4080
ttggttgacg gcaatttcga tgatgcagct tgggcgcagg tcgatgcga cgcaatcgtc    4140 cgatccggag ccgggactgt cgggcgtaca caaatcgccc gcagaagcgc ggccgtctgg    4200
accgatggct gtgtagaagt actcgccgat agtggaaacc gacgcccag cactcgtccg    4260 agggcaaagg aatagcacgt gctacgagat ttcgattcca ccgccgcctt ctatgaaagg    4320
ttgggcttcg gaatcgtttt ccgggacgcc ggctggatga tcctccagcg cggggatctc    4380
atgctggagt cttcgcccca ccccaacttg tttattgcag cttataatgg ttacaaataa    4440
agcaatagca tcacaaattt cacaaataaa gcattttttt cactgcattc tagttgtggt    4500
ttgtccaaac tcatcaatgt atcttatcat gtctgtatac cgtcgacctc tagctagagc    4560
ttggcgtaat catggtcata gctgtttcct gtgtgaaatt gttatccgct cacaattcca    4620
cacaacatac gagccggaag cataaagtgt aaagcctggg gtgcctaatg agtgagctaa    4680
ctcacattaa ttgcgttgcg ctcactgccc gctttccagt cgggaaacct gtcgtgccag    4740
ctgcattaat gaatcggcca acgcgcgggg agaggcggtt tgcgtattgg gcgctcttcc    4800
gcttcctcgc tcactgactc gctgcgctcg gtcgttcggc tgcggcgagc ggtatcagct    4860
cactcaaagg cggtaatacg gttatccaca gaatcagggg ataacgcagg aaagaacatg    4920
tgagcaaaag gccagcaaaa ggccaggaac cgtaaaaagg ccgcgttgct ggcgtttttc    4980
cataggctcc gcccccctga cgagcatcac aaaaatcgac gctcaagtca gaggtggcga    5040
aacccgacag gactataaag ataccaggcg tttccccctg gaagctccct cgtgcgctct    5100
cctgttccga ccctgccgct taccggatac ctgtccgcct ttctcccttc gggaagcgtg    5160
gcgctttctc atagctcacg ctgtaggtat ctcagttcgg tgtaggtcgt tcgctccaag    5220
```

```
ctgggctgtg tgcacgaacc ccccgttcag cccgaccgct gcgccttatc cggtaactat    5280
cgtcttgagt ccaacccggt aagacacgac ttatcgccac tggcagcagc cactggtaac    5340
aggattagca gagcgaggta tgtaggcggt gctacagagt tcttgaagtg gtggcctaac    5400
tacggctaca ctagaagaac agtatttggt atctgcgctc tgctgaagcc agttaccttc    5460 ggaaaagag ttggtagctc ttgatccggc aaacaaacca ccgctggtag cggtttttttt    5520 gtttgcaagc agcagattac gcgcagaaaa aaggatctc aagaagatcc tttgatcttt     5580
tctacggggt ctgacgctca gtggaacgaa aactcacgtt aagggatttt ggtcatgaga    5640
ttatcaaaaa ggatcttcac ctagatcctt taaattaaa aatgaagttt taaatcaatc     5700
taaagtatat atgagtaaac ttggtctgac agttaccaat gcttaatcag tgaggcacct    5760
atctcagcga tctgtctatt tcgttcatcc atagttgcct gactccccgt cgtgtagata    5820
actacgatac gggagggctt accatctggc cccagtgctg caatgatacc gcgagaccca    5880
cgctcaccgg ctccagattt atcagcaata aaccagccag ccggaagggc cgagcgcaga    5940
agtggtcctg caactttatc cgcctccatc cagtctatta attgttgccg ggaagctaga    6000
gtaagtagtt cgccagttaa tagtttgcgc aacgttgttg ccattgctac aggcatcgtg    6060
gtgtcacgct cgtcgtttgg tatggcttca ttcagctccg gttcccaacg atcaaggcga    6120
gttacatgat cccccatgtt gtgcaaaaaa gcggttagct ccttcggtcc tccgatcgtt    6180
gtcagaagta agttggccgc agtgttatca ctcatggtta tggcagcact gcataattct    6240
cttactgtca tgccatccgt aagatgcttt tctgtgactg gtgagtactc aaccaagtca    6300
ttctgagaat agtgtatgcg gcgaccgagt tgctcttgcc cggcgtcaat acgggataat    6360
accgcgccac atagcagaac tttaaaagtg ctcatcattg gaaaacgttc ttcggggcga    6420
aaactctcaa ggatcttacc gctgttgaga tccagttcga tgtaacccac tcgtgcaccc    6480
aactgatctt cagcatcttt tactttcacc agcgtttctg ggtgagcaaa aacaggaagg    6540
caaaatgccg caaaaaaggg aataagggcg acacggaaat gttgaatact catactcttc    6600
ctttttcaat attattgaag catttatcag ggttattgtc tcatgagcgg atacatattt    6660
gaatgtattt agaaaaataa acaaataggg gttccgcgca catttccccg aaaagtgcca    6720
cctgacgtc                                                            6729
```

<210> SEQ ID NO 22
<211> LENGTH: 6714
<212> TYPE: DNA
<213> ORGANISM: artificial
<220> FEATURE:
<223> OTHER INFORMATION: expression vector coding for ICOS-msFc

<400> SEQUENCE: 22

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca caaggcaag gcttgaccga caattgcatg aagaatctgc     180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
```

-continued

| | |
|---|---|
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctgtctaga | 900 |
| tgccaccatg gctggagcc tgatcctcct gttcctcgtc gctgtggcta caggtaaggg | 960 |
| gctcacagta gcaggcttga ggtctggaca tatatatggg tgacaatgac atccactttg | 1020 |
| cctttctctc cacaggtggc gcgcatgccg aaatcaatgg ttctgccaat tatgagatgt | 1080 |
| ttatatttca caacggaggt gtacaaattt tatgcaaata tcctgacatt gtccagcaat | 1140 |
| ttaaaatgca gttgctgaaa gggggcaaa tactctgcga tctcactaag acaaaaggaa | 1200 |
| gtggaaacac agtgtccatt aagagtctga aattctgcca ttctcagtta ccaacaaca | 1260 |
| gtgtctcttt ttttctatac aacttggacc attctcatgc caactattac ttctgcaacc | 1320 |
| tatcaatttt tgatcctcct ccttttaaag taactcttac aggaggatat ttgcatattt | 1380 |
| atgaatcaca acttgctagc ggttgtaagc cttgcatatg tacagtccca gaagtatcat | 1440 |
| ctgtcttcat cttcccccca aagcccaagg atgtgctcac cattactctg actcctaagg | 1500 |
| tcacgtgtgt tgtggtagac atcagcaagg atgatcccga ggtccagttc agctggtttg | 1560 |
| tagatgatgt ggaggtgcac acagctcaga cgaaacccg ggaggagcag atcaacagca | 1620 |
| ctttccgttc agtcagtgaa cttcccatca tgcaccagga ctggctcaat ggcaaggagt | 1680 |
| tcaaatgcag ggtcaacagt gcagctttcc ctgcccccat cgagaaaacc atctccaaaa | 1740 |
| ccaaaggcag accgaaggct ccacaggtgt acaccattcc acctcccaag gagcagatgg | 1800 |
| ccaaggataa agtcagtctg acctgcatga taacaaactt cttccctgaa gacattactg | 1860 |
| tggagtggca gtggaatggg cagccagcgg agaactacaa gaacactcag cccatcatgg | 1920 |
| acacagatgg ctcttacttc gtctacagca agctcaatgt gcagaagagc aactgggagg | 1980 |
| caggaaatac tttcacctgc tctgtgttac atgagggcct gcacaaccac catactgaga | 2040 |
| agagcctctc ccactctcct ggtaaaacta gtggcaaacc aatcccaaac ccactgctgg | 2100 |
| gcctggatag tacttaaaag cttaaacccg ctgatcagcc tcgactgtgc cttctagttg | 2160 |
| ccagccatct gttgtttgcc cctccccgt gccttcctg accctggaag gtgccactcc | 2220 |
| cactgtcctt tcctaataaa atgaggaaat tgcatcgcat tgtctgagta ggtgtcattc | 2280 |
| tattctgggg ggtggggtgg ggcaggacag caagggggag gattgggaag acaatagcag | 2340 |
| gcatgctggg gatgcggtgg gctctatggc ttctgaggcg gaaagaacca gctgggctc | 2400 |
| taggggtat ccccacgcgc cctgtagcgg cgcattaagc gcggcgggtg tggtggttac | 2460 |
| gcgcagcgtg accgctacac ttgccagcgc cctagcgccc gctccttcg ctttcttccc | 2520 |
| ttcctttctc gccacgttcg ccggctttcc ccgtcaagct ctaaatcggg ggctcccttt | 2580 |
| agggttccga tttagtgctt tacggcacct cgaccccaaa aaacttgatt agggtgatgg | 2640 |
| ttcacgtagt gggccatcgc cctgatagac ggttttttcgc cctttgacgt tggagtccac | 2700 |
| gttctttaat agtggactct tgttccaaac tggaacaaca ctcaaccta tctcggtcta | 2760 |
| ttcttttgat ttataaggga ttttgccgat ttcggcctat tggttaaaaa atgagctgat | 2820 |
| ttaacaaaaa tttaacgcga attaattctg tggaatgtgt gtcagttagg gtgtggaaag | 2880 |

```
tccccaggct ccccagcagg cagaagtatg caaagcatgc atctcaatta gtcagcaacc    2940
aggtgtggaa agtccccagg ctccccagca ggcagaagta tgcaaagcat gcatctcaat    3000
tagtcagcaa ccatagtccc gcccctaact ccgcccatcc cgcccctaac tccgcccagt    3060
tccgcccatt ctccgcccca tggctgacta atttttttta tttatgcaga ggccgaggcc    3120
gcctctgcct ctgagctatt ccagaagtag tgaggaggct ttttggagg cctaggcttt     3180 tgcaaaaagc tcccgggagc ttgtatatcc attttcggat ctgatcagca cgtgatgaaa    3240
aagcctgaac tcaccgcgac gtctgtcgag aagtttctga tcgaaaagtt cgacagcgtc    3300
tccgacctga tgcagctctc ggagggcgaa gaatctcgtg ctttcagctt cgatgtagga    3360
gggcgtggat atgtcctgcg ggtaaatagc tgcgccgatg gtttctacaa agatcgttat    3420
gtttatcggc actttgcatc ggccgcgctc ccgattccgg aagtgcttga cattggggaa    3480
ttcagcgaga gcctgaccta ttgcatctcc cgccgtgcac agggtgtcac gttgcaagac    3540
ctgcctgaaa ccgaactgcc cgctgttctg cagccggtcg cggaggccat ggatgcgatc    3600
gctgcggccg atcttagcca gacgagcggg ttcgcccat tcggaccgca aggaatcggt     3660
caatacacta catggcgtga tttcatatgc gcgattgctg atccccatgt gtatcactgg    3720
caaactgtga tggacgacac cgtcagtgcg tccgtcgcgc aggctctcga tgagctgatg    3780
ctttgggccg aggactgccc cgaagtccgg cacctcgtgc acgcggattt cggctccaac    3840
aatgtcctga cggacaatgg ccgcataaca gcggtcattg actggagcga ggcgatgttc    3900
ggggattccc aatacgaggt cgccaacatc ttcttctgga ggccgtggtt ggcttgtatg    3960
gagcagcaga cgcgctactt cgagcggagg catccggagc ttgcaggatc gccgcggctc    4020
cgggcgtata tgctccgcat tggtcttgac caactctatc agagcttggt tgacggcaat    4080
ttcgatgatg cagcttgggc gcagggtcga tgcgacgcaa tcgtccgatc cggagccggg    4140
actgtcgggc gtacacaaat cgcccgcaga agcgcggccg tctggaccga tggctgtgta    4200
gaagtactcg ccgatagtgg aaaccgacgc cccagcactc gtccgagggc aaaggaatag    4260
cacgtgctac gagatttcga ttccaccgcc gccttctatg aaaggttggg cttcggaatc    4320
gttttccggg acgccggctg gatgatcctc cagcgcgggg atctcatgct ggagttcttc    4380
gcccacccca acttgtttat tgcagcttat aatggttaca aataaagcaa tagcatcaca    4440
aatttcacaa ataaagcatt tttttcactg cattctagtt gtggtttgtc caaactcatc    4500
aatgtatctt atcatgtctg tataccgtcg acctctagct agagcttggc gtaatcatgg    4560
tcatagctgt ttcctgtgtg aaattgttat ccgctcacaa ttccacacaa catacgagcc    4620
ggaagcataa agtgtaaagc ctggggtgcc taatgagtga gctaactcac attaattgcg    4680
ttgcgctcac tgcccgcttt ccagtcggga acctgtcgt gccagctgca ttaatgaatc     4740
ggccaacgcg cggggagagg cggtttgcgt attgggcgct cttccgcttc ctcgctcact    4800
gactcgctgc gctcggtcgt tcggctgcgg cgagcggtat cagctcactc aaaggcggta    4860
atacggttat ccacagaatc aggggataac gcaggaaaga acatgtgagc aaaaggccag    4920
caaaaggcca ggaaccgtaa aaaggccgcg ttgctggcgt ttttccatag gctccgcccc    4980
cctgacgagc atcacaaaaa tcgacgctca agtcagaggt ggcgaaaccc gacaggacta    5040
taaagatacc aggcgtttcc ccctggaagc tccctcgtgc gctctcctgt tccgaccctg    5100
ccgcttaccg gatacctgtc cgcctttctc ccttcgggaa gcgtggcgct ttctcatagc    5160
tcacgctgta ggtatctcag ttcggtgtag gtcgttcgct ccaagctggg ctgtgtgcac    5220
```

```
gaacccccg ttcagcccga ccgctgcgcc ttatccggta actatcgtct tgagtccaac    5280
ccggtaagac acgacttatc gccactggca gcagccactg gtaacaggat tagcagagcg    5340
aggtatgtag gcggtgctac agagttcttg aagtggtggc ctaactacgg ctacactaga    5400
agaacagtat ttggtatctg cgctctgctg aagccagtta ccttcggaaa aagagttggt    5460
agctcttgat ccggcaaaca accaccgct ggtagcggtt ttttgtttg caagcagcag       5520 attacgcgca gaaaaaaagg atctcaagaa gatcctttga tcttttctac ggggtctgac    5580
gctcagtgga acgaaaactc acgttaaggg attttggtca tgagattatc aaaaggatc     5640 ttcacctaga tccttttaaa ttaaaaatga agttttaaat caatctaaag tatatatgag    5700
taaacttggt ctgacagtta ccaatgctta atcagtgagg cacctatctc agcgatctgt    5760
ctatttcgtt catccatagt tgcctgactc cccgtcgtgt agataactac gatacgggag    5820
ggcttaccat ctggccccag tgctgcaatg ataccgcgag acccacgctc accggctcca    5880
gatttatcag caataaacca gccagccgga agggccgagc gcagaagtgg tcctgcaact    5940
ttatccgcct ccatccagtc tattaattgt tgccgggaag ctagagtaag tagttcgcca    6000
gttaatagtt tgcgcaacgt tgttgccatt gctacaggca tcgtggtgtc acgctcgtcg    6060
tttggtatgg cttcattcag ctccggttcc caacgatcaa ggcgagttac atgatccccc    6120
atgttgtgca aaaaagcggt tagctccttc ggtcctccga tcgttgtcag aagtaagttg    6180
gccgcagtgt tatcactcat ggttatggca gcactgcata attctcttac tgtcatgcca    6240
tccgtaagat gcttttctgt gactggtgag tactcaacca agtcattctg agaatagtgt    6300
atgcggcgac cgagttgctc ttgcccggcg tcaatacggg ataataccgc gccacatagc    6360
agaactttaa aagtgctcat cattggaaaa cgttcttcgg ggcgaaaact ctcaaggatc    6420
ttaccgctgt tgagatccag ttcgatgtaa cccactcgtg cacccaactg atcttcagca    6480
tcttttactt tcaccagcgt ttctgggtga gcaaaaacag gaaggcaaaa tgccgcaaaa    6540
aagggaataa gggcgacacg gaaatgttga atactcatac tcttcctttt tcaatattat    6600
tgaagcattt atcagggtta ttgtctcatg agcggataca tatttgaatg tatttagaaa    6660
aataaacaaa tagggggttcc gcgcacattt ccccgaaaag tgccacctga cgtc         6714
```

<210> SEQ ID NO 23
<211> LENGTH: 6729
<212> TYPE: DNA
<213> ORGANISM: artificial
<220> FEATURE:
<223> OTHER INFORMATION: expression vector coding for F119SICOS-Fc

<400> SEQUENCE: 23

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

-continued

```
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctgtctaga      900
tgccaccatg ggctggagcc tgatcctcct gttcctcgtc gctgtggcta caggtaaggg      960
gctcacagta gcaggcttga ggtctggaca tatatatggg tgacaatgac atccactttg     1020
cctttctctc cacaggtggc gcgcatgccg aaatcaatgg ttctgccaat tatgagatgt     1080
ttatatttca aacggaggt gtacaaattt tatgcaaata tcctgacatt gtccagcaat     1140
ttaaaatgca gttgctgaaa gggggcaaa tactctgcga tctcactaag acaaaaggaa     1200
gtggaaacac agtgtccatt aagagtctga aattctgcca ttctcagtta ccaacaaca     1260 gtgtctcttt ttttctatac aacttggacc attctcatgc aactattac ttctgcaacc     1320 tatcaatttt tgatcctcct ccttctaaag taactcttac aggaggatat ttgcatattt     1380
atgaatcaca acttgctagc gacaaaactc acacatgccc accgtgccca gcacctgaac     1440
tcctgggggg accgtcagtc ttcctcttcc ccccaaaacc caaggacacc ctcatgatct     1500
cccggacccc tgaggtcaca tgcgtggtgg tggacgtgag ccacgaagac cctgaggtca     1560
agttcaactg gtacgtggac ggcgtggagg tgcataatgc caagacaaag ccgcgggagg     1620
agcagtacaa cagcacgtac cgtgtggtca gcgtcctcac cgtcctgcac caggactggc     1680
tgaatggcaa ggagtacaag tgcaaggtct ccaacaaagc cctcccagcc cccatcgaga     1740
aaaccatctc caaagccaaa gggcagcccc gagaaccaca ggtgtacacc ctgcccccat     1800
cccgggagga gatgaccaag aaccaggtca gcctgacctg cctggtcaaa ggcttctatc     1860
ccagcgacat cgccgtggag tgggagagca atgggcagcc ggagaacaac tacaagacca     1920
cgcctcccgt gctggactcc gacggctcct tcttcctcta tagcaagctc accgtggaca     1980
agagcaggtg gcagcagggg aacgtcttct catgctccgt gatgcatgag gctctgcaca     2040
accactacac gcagaagagc ctctccctgt ccccgggtaa aactagtggc aaaccaatcc     2100
caaacccact gctgggcctg gatagtactt aaaagcttaa acccgctgat cagcctcgac     2160
tgtgccttct agttgccagc catctgttgt ttgcccctcc ccgtgccttc cttgaccctg     2220
ggaaggtgcc actcccactg tcctttccta ataaaatgag gaaattgcat cgcattgtct     2280
gagtaggtgt cattctattc tggggggtgg ggtggggcag gacagcaagg gggaggattg     2340
ggaagacaat agcaggcatg ctggggatgc ggtgggctct atggcttctg aggcggaaag     2400
aaccagctgg ggctctaggg ggtatcccca cgcgccctgt agcggcgcat taagcgcggc     2460
gggtgtggtg gttacgcgca gcgtgaccgc tacacttgcc agcgccctag cgcccgctcc     2520
tttcgctttc ttcccttcct ttctcgccac gttcgccggc tttccccgtc aagctctaaa     2580 tcggggctc cctttagggt tccgatttag tgctttacgg cacctcgacc ccaaaaaact     2640 tgattaggt gatggttcac gtagtgggcc atcgccctga tagacggttt ttcgcccttt     2700
gacgttggag tccacgttct ttaatagtgg actcttgttc caaactggaa caacactcaa     2760
ccctatctcg gtctattctt ttgatttata agggattttg ccgatttcgg cctattggtt     2820
aaaaaatgag ctgatttaac aaaaatttaa cgcgaattaa ttctgtggaa tgtgtgtcag     2880
ttagggtgtg gaaagtcccc aggctcccca gcaggcagaa gtatgcaaag catgcatctc     2940
```

```
aattagtcag caaccaggtg tggaaagtcc ccaggctccc cagcaggcag aagtatgcaa    3000
agcatgcatc tcaattagtc agcaaccata gtcccgcccc taactccgcc catcccgccc    3060
ctaactccgc ccagttccgc ccattctccg ccccatggct gactaatttt ttttatttat    3120
gcagaggccg aggccgcctc tgcctctgag ctattccaga agtagtgagg aggcttttt     3180 ggaggcctag gcttttgcaa aaagctcccg ggagcttgta tatccatttt cggatctgat    3240
cagcacgtga tgaaaaagcc tgaactcacc gcgacgtctg tcgagaagtt tctgatcgaa    3300
aagttcgaca gcgtctccga cctgatgcag ctctcggagg gcgaagaatc tcgtgctttc    3360
agcttcgatg taggagggcg tggatatgtc ctgcgggtaa atagctgcgc cgatggtttc    3420
tacaaagatc gttatgttta tcggcacttt gcatcggccg cgctcccgat tccggaagtg    3480
cttgacattg gggaattcag cgagagcctg acctattgca tctcccgccg tgcacagggt    3540
gtcacgttgc aagacctgcc tgaaaccgaa ctgcccgctg ttctgcagcc ggtcgcggag    3600
gccatggatg cgatcgctgc ggccgatctt agccagacga gcgggttcgg cccattcgga    3660
ccgcaaggaa tcggtcaata cactacatgg cgtgatttca tatgcgcgat tgctgatccc    3720
catgtgtatc actggcaaac tgtgatggac gacaccgtca gtgcgtccgt cgcgcaggct    3780
ctcgatgagc tgatgctttg gccgaggac tgccccgaag tccggcacct cgtgcacgcg     3840
gatttcggct ccaacaatgt cctgacggac aatggccgca taacagcggt cattgactgg    3900
agcgaggcga tgttcgggga ttcccaatac gaggtcgcca acatcttctt ctggaggccg    3960
tggttggctt gtatggagca gcagacgcgc tacttcgagc ggaggcatcc ggagcttgca    4020
ggatcgccgc ggctccgggc gtatatgctc cgcattggtc ttgaccaact ctatcagagc    4080
ttggttgacg gcaatttcga tgatgcagct tgggcgcagg gtcgatgcga cgcaatcgtc    4140
cgatccggag ccgggactgt cgggcgtaca caaatcgccc gcagaagcgc ggccgtctgg    4200
accgatggct gtgtagaagt actcgccgat agtggaaacc gacgcccag cactcgtccg     4260 agggcaaagg aatagcacgt gctacgagat ttcgattcca ccgccgcctt ctatgaaagg    4320
ttgggcttcg gaatcgtttt ccgggacgcc ggctggatga tcctccagcg cggggatctc    4380
atgctggagt cttcgcccca ccccaacttg tttattgcag cttataatgg ttacaaataa    4440
agcaatagca tcacaaattt cacaaataaa gcattttttt cactgcattc tagttgtggt    4500
ttgtccaaac tcatcaatgt atcttatcat gtctgtatac cgtcgacctc tagctagagc    4560
ttggcgtaat catggtcata gctgtttcct gtgtgaaatt gttatccgct cacaattcca    4620
cacaacatac gagccggaag cataaagtgt aaagcctggg gtgcctaatg agtgagctaa    4680
ctcacattaa ttgcgttgcg ctcactgccc gctttccagt cgggaaacct gtcgtgccag    4740
ctgcattaat gaatcggcca acgcgcgggg agaggcggtt tgcgtattgg gcgctcttcc    4800
gcttcctcgc tcactgactc gctgcgctcg gtcgttcggc tgcggcgagc ggtatcagct    4860
cactcaaagg cggtaatacg gttatccaca gaatcagggg ataacgcagg aaagaacatg    4920
tgagcaaaag gccagcaaaa ggccaggaac cgtaaaaagg ccgcgttgct ggcgtttttc    4980
cataggctcc gcccccctga cgagcatcac aaaaatcgac gctcaagtca gaggtggcga    5040
aacccgacag gactataaag ataccaggcg tttccccctg gaagctccct cgtgcgctct    5100
cctgttccga ccctgccgct taccggatac ctgtccgcct ttctcccttc gggaagcgtg    5160
gcgctttctc atagctcacg ctgtaggtat ctcagttcgg tgtaggtcgt tcgctccaag    5220
ctgggctgtg tgcacgaacc ccccgttcag cccgaccgct gcgccttatc cggtaactat    5280
cgtcttgagt ccaacccggt aagacacgac ttatcgccac tggcagcagc cactggtaac    5340
```

```
aggattagca gagcgaggta tgtaggcggt gctacagagt tcttgaagtg gtggcctaac    5400
tacggctaca ctagaagaac agtatttggt atctgcgctc tgctgaagcc agttaccttc    5460
ggaaaaagag ttggtagctc ttgatccggc aaacaaacca ccgctggtag cggttttttt    5520
gtttgcaagc agcagattac gcgcagaaaa aaaggatctc aagaagatcc tttgatcttt    5580
tctacggggt ctgacgctca gtggaacgaa aactcacgtt aagggatttt ggtcatgaga    5640
ttatcaaaaa ggatcttcac ctagatcctt taaattaaa aatgaagttt taaatcaatc    5700
taaagtatat atgagtaaac ttggtctgac agttaccaat gcttaatcag tgaggcacct    5760
atctcagcga tctgtctatt tcgttcatcc atagttgcct gactccccgt cgtgtagata    5820
actacgatac gggagggctt accatctggc cccagtgctg caatgatacc gcgagaccca    5880
cgctcaccgg ctccagattt atcagcaata aaccagccag ccggaagggc cgagcgcaga    5940
agtggtcctg caactttatc cgcctccatc cagtctatta attgttgccg ggaagctaga    6000
gtaagtagtt cgccagttaa tagtttgcgc aacgttgttg ccattgctac aggcatcgtg    6060
gtgtcacgct cgtcgtttgg tatggcttca ttcagctccg gttcccaacg atcaaggcga    6120
gttacatgat cccccatgtt gtgcaaaaaa gcggttagct ccttcggtcc tccgatcgtt    6180
gtcagaagta agttggccgc agtgttatca ctcatggtta tggcagcact gcataattct    6240
cttactgtca tgccatccgt aagatgcttt tctgtgactg gtgagtactc aaccaagtca    6300
ttctgagaat agtgtatgcg gcgaccgagt tgctcttgcc cggcgtcaat acgggataat    6360
accgcgccac atagcagaac tttaaaagtg ctcatcattg gaaaacgttc ttcggggcga    6420
aaactctcaa ggatcttacc gctgttgaga tccagttcga tgtaacccac tcgtgcaccc    6480
aactgatctt cagcatcttt tactttcacc agcgtttctg ggtgagcaaa aacaggaagg    6540
caaaatgccg caaaaaaggg aataagggcg acacggaaat gttgaatact catactcttc    6600
ctttttcaat attattgaag catttatcag ggttattgtc tcatgagcgg atacatattt    6660
gaatgtattt agaaaaataa acaaataggg gttccgcgca catttccccg aaaagtgcca    6720
cctgacgtc                                                           6729
```

<210> SEQ ID NO 24
<211> LENGTH: 389
<212> TYPE: PRT
<213> ORGANISM: artificial
<220> FEATURE:
<223> OTHER INFORMATION: msICOS-huFc

<400> SEQUENCE: 24

```
Met Gly Trp Ser Leu Ile Leu Leu Phe Leu Val Ala Val Ala Thr Gly
1               5                   10                  15

Gly Ala His Ala Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110
```

Ile Phe Asp Pro Pro Phe Gln Glu Arg Asn Leu Ser Gly Gly Tyr
        115                 120                 125

Leu His Ile Tyr Glu Ser Gln Leu Cys Cys Gln Leu Lys Leu Trp Leu
    130                 135                 140

Ala Ser Asp Lys Thr His Thr Cys Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly Lys Thr Ser Gly Lys Pro Ile Pro Asn Pro Leu Leu
    370                 375                 380

Gly Leu Asp Ser Thr
385

<210> SEQ ID NO 25
<211> LENGTH: 6756
<212> TYPE: DNA
<213> ORGANISM: artificial
<220> FEATURE:
<223> OTHER INFORMATION: expression vector coding for msICOS-huFc

<400> SEQUENCE: 25
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacgggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420

| | |
|---|---|
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctgtctaga | 900 |
| tgccaccatg gctggagcc tgatcctcct gttcctcgtc gctgtggcta caggtaaggg | 960 |
| gctcacagta gcaggcttga ggtctggaca tatatatggg tgacaatgac atccactttg | 1020 |
| cctttctctc cacaggtggc gcgcatgccg aaatcaatgg ctcggccgat cataggatgt | 1080 |
| tttcatttca caatgaggt gtacagattt cttgtaaata ccctgagact gtccagcagt | 1140 |
| taaaaatgcg attgttcaga gagagagaag tcctctgcga actcaccaag accaagggaa | 1200 |
| gcggaaatgc ggtgtccatc aagaatccaa tgctctgtct atatcatctg tcaaacaaca | 1260 |
| gcgtctcttt tttcctaaac aacccagaca gctcccaggg aagctattac ttctgcagcc | 1320 |
| tgtccatttt tgacccacct cctttcaag aaggaacct tagtggagga tatttgcata | 1380 |
| tttatgaatc ccagctctgc tgccagctga agctctggct agctagcgac aaaactcaca | 1440 |
| catgcccacc gtgcccagca cctgaactcc tggggggacc gtcagtcttc ctcttccccc | 1500 |
| caaaacccaa ggacaccctc atgatctccc ggacccctga ggtcacatgc gtggtggtgg | 1560 |
| acgtgagcca cgaagaccct gaggtcaagt tcaactggta cgtggacggc gtggaggtgc | 1620 |
| ataatgccaa gacaaagccg cgggaggagc agtacaacag cacgtaccgt gtggtcagcg | 1680 |
| tcctcaccgt cctgcaccag gactggctga atggcaagga gtacaagtgc aaggtctcca | 1740 |
| acaaagccct cccagccccc atcgagaaaa ccatctccaa agccaaaggg cagccccgag | 1800 |
| aaccacaggt gtacaccctg cccccatccc gggaggagat gaccaagaac caggtcagcc | 1860 |
| tgacctgcct ggtcaaaggc ttctatccca gcgacatcgc cgtggagtgg gagagcaatg | 1920 |
| ggcagccgga gaacaactac aagaccacgc ctcccgtgct ggactccgac ggctccttct | 1980 |
| tcctctatag caagctcacc gtggacaaga gcaggtggca gcaggggaac gtcttctcat | 2040 |
| gctccgtgat gcatgaggct ctgcacaacc actacacgca gaagagcctc tccctgtccc | 2100 |
| cgggtaaaac tagtggcaaa ccaatcccaa acccactgct gggcctggat agtacttaaa | 2160 |
| agcttaaacc cgctgatcag cctcgactgt gccttctagt tgccagccat ctgttgtttg | 2220 |
| cccctccccc gtgccttcct tgaccctgga aggtgccact cccactgtcc tttcctaata | 2280 |
| aaatgaggaa attgcatcgc attgtctgag taggtgtcat tctattctgg ggggtggggt | 2340 |
| ggggcaggac agcaagggg aggattggga agacaatagc aggcatgctg gggatgcggt | 2400 |
| gggctctatg gcttctgagg cggaaagaac cagctggggc tctaggggt atccccacgc | 2460 |
| gccctgtagc ggcgcattaa gcgcggcggg tgtggtggtt acgcgcagcg tgaccgctac | 2520 |
| acttgccagc gccctagcgc ccgctccttt cgctttcttc ccttcctttc tcgccacgtt | 2580 |
| cgccggcttt ccccgtcaag ctctaaatcg ggggctccct ttagggttcc gatttagtgc | 2640 |
| tttacggcac ctcgacccca aaaaacttga ttagggtgat ggttcacgta gtgggccatc | 2700 |
| gccctgatag acggtttttc gccctttgac gttggagtcc acgttcttta atagtggact | 2760 |
| cttgttccaa actggaacaa cactcaaccc tatctcggtc tattcttttg atttataagg | 2820 |

```
gattttgccg atttcggcct attggttaaa aaatgagctg atttaacaaa aatttaacgc    2880
gaattaattc tgtggaatgt gtgtcagtta gggtgtggaa agtccccagg ctccccagca    2940
ggcagaagta tgcaaagcat gcatctcaat tagtcagcaa ccaggtgtgg aaagtcccca    3000
ggctccccag caggcagaag tatgcaaagc atgcatctca attagtcagc aaccatagtc    3060
ccgcccctaa ctccgcccat cccgccccta actccgccca gttccgccca ttctccgccc    3120
catggctgac taatttttt tatttatgca gaggccgagg ccgcctctgc ctctgagcta    3180
ttccagaagt agtgaggagg cttttttgga ggcctaggct tttgcaaaaa gctcccggga    3240
gcttgtatat ccatttcgg atctgatcag cacgtgatga aaaagcctga actcaccgcg    3300
acgtctgtcg agaagtttct gatcgaaaag ttcgacagcg tctccgacct gatgcagctc    3360
tcggagggcg aagaatctcg tgctttcagc ttcgatgtag agggcgtgg atatgtcctg    3420 cgggtaaata gctgcgccga tggtttctac aaagatcgtt atgtttatcg gcactttgca    3480
tcggccgcgc tcccgattcc ggaagtgctt gacattgggg aattcagcga gagcctgacc    3540
tattgcatct cccgccgtgc acagggtgtc acgttgcaag acctgcctga aaccgaactg    3600
cccgctgttc tgcagccggt cgcggaggcc atggatgcga tcgctgcggc cgatcttagc    3660
cagacgagcg ggttcggccc attcggaccg caaggaatcg gtcaatacac tacatggcgt    3720
gatttcatat gcgcgattgc tgatccccat gtgtatcact ggcaaactgt gatggacgac    3780
accgtcagtg cgtccgtcgc gcaggctctc gatgagctga tgctttgggc cgaggactgc    3840
cccgaagtcc ggcacctcgt gcacgcggat ttcggctcca acaatgtcct gacgacaat    3900 ggccgcataa cagcggtcat tgactggagc gaggcgatgt tcgggattc ccaatacgag    3960 gtcgccaaca tcttcttctg gaggccgtgg ttggcttgta tggagcagca gacgcgctac    4020
ttcgagcgga ggcatccgga gcttgcagga tcgccgcggc tccgggcgta tgctccgc    4080 attggtcttg accaactcta tcagagcttg gttgacggca atttcgatga tgcagcttgg    4140
gcgcagggtc gatgcgacgc aatcgtccga tccggagccg ggactgtcgg gcgtacacaa    4200
atcgcccgca gaagcgcggc cgtctggacc gatggctgtg tagaagtact cgccgatagt    4260
ggaaaccgac gccccagcac tcgtccgagg gcaaaggaat agcacgtgct acgagatttc    4320
gattccaccg ccgccttcta tgaaaggttg ggcttcggaa tcgttttccg gacgccggc    4380 tggatgatcc tccagcgcgg ggatctcatg ctggagttct tcgcccaccc caacttgttt    4440
attgcagctt ataatggtta caaataaagc aatagcatca caaatttcac aaataaagca    4500 ttttttcac tgcattctag ttgtggtttg tccaaactca tcaatgtatc ttatcatgtc    4560
tgtataccgt cgacctctag ctagagcttg gcgtaatcat ggtcatagct gtttcctgtg    4620
tgaaattgtt atccgctcac aattccacac aacatacgag ccgaagcat aaagtgtaaa    4680 gcctggggtg cctaatgagt gagctaactc acattaattg cgttgcgctc actgcccgct    4740
ttccagtcgg gaaacctgtc gtgccagctg cattaatgaa tcggccaacg cgcgggaga    4800 ggcggtttgc gtattgggcg ctcttccgct tcctcgctca ctgactcgct gcgctcggtc    4860
gttcggctgc ggcgagcggt atcagctcac tcaaaggcgg taatacggtt atccacagaa    4920 tcagggata acgcaggaaa gaacatgtga gcaaaaggcc agcaaaaggc caggaaccgt    4980
aaaaaggccg cgttgctggc gtttttccat aggctccgcc ccctgacga gcatcacaaa    5040 aatcgacgct caagtcagag gtggcgaaac ccgacaggac tataaagata ccaggcgttt    5100
ccccctggaa gctccctcgt gcgctctcct gttccgaccc tgccgcttac cggatacctg    5160
```

-continued

```
tccgcctttc tcccttcggg aagcgtggcg ctttctcata gctcacgctg taggtatctc    5220
agttcggtgt aggtcgttcg ctccaagctg ggctgtgtgc acgaaccccc cgttcagccc    5280
gaccgctgcg ccttatccgg taactatcgt cttgagtcca acccgtaag  acacgactta    5340
tcgccactgg cagcagccac tggtaacagg attagcagag cgaggtatgt aggcggtgct    5400
acagagttct tgaagtggtg gcctaactac ggctacacta aagaacagt  atttggtatc    5460
tgcgctctgc tgaagccagt taccttcgga aaaagagttg gtagctcttg atccggcaaa    5520
caaaccaccg ctggtagcgg ttttttttgtt tgcaagcagc agattacgcg cagaaaaaaa    5580
ggatctcaag aagatccttt gatcttttct acggggtctg acgctcagtg aacgaaaac    5640
tcacgttaag ggattttggt catgagatta tcaaaaagga tcttcaccta gatccttta    5700
aattaaaaat gaagttttaa atcaatctaa agtatatatg agtaaacttg gtctgacagt    5760
taccaatgct taatcagtga ggcacctatc tcagcgatct gtctatttcg ttcatccata    5820
gttgcctgac tccccgtcgt gtagataact acgatacggg agggcttacc atctggcccc    5880
agtgctgcaa tgataccgcg agacccacgc tcaccggctc cagatttatc agcaataaac    5940
cagccagccg aagggccga  gcgcagaagt ggtcctgcaa ctttatccgc ctccatccag    6000
tctattaatt gttgccggga agctagagta agtagttcgc cagttaatag tttgcgcaac    6060
gttgttgcca ttgctacagg catcgtggtg tcacgctcgt cgtttggtat ggcttcattc    6120
agctccggtt cccaacgatc aaggcgagtt acatgatccc ccatgttgtg caaaaaagcg    6180
gttagctcct tcggtcctcc gatcgttgtc agaagtaagt tggccgcagt gttatcactc    6240
atggttatgg cagcactgca taattctctt actgtcatgc catccgtaag atgcttttct    6300
gtgactggtg agtactcaac caagtcattc tgagaatagt gtatgcggcg accgagttgc    6360
tcttgcccgg cgtcaatacg ggataatacc gcgccacata gcagaacttt aaaagtgctc    6420
atcattggaa aacgttcttc ggggcgaaaa ctctcaagga tcttaccgct gttgagatcc    6480
agttcgatgt aacccactcg tgcacccaac tgatcttcag catcttttac tttcaccagc    6540
gtttctgggt gagcaaaaac aggaaggcaa aatgccgcaa aaaagggaat aagggcgaca    6600
cggaaatgtt gaatactcat actcttcctt tttcaatatt attgaagcat ttatcagggt    6660
tattgtctca tgagcggata catatttgaa tgtatttaga aaaataaaca aataggggtt    6720
ccgcgcacat ttccccgaaa agtgccacct gacgtc                              6756
```

<210> SEQ ID NO 26
<211> LENGTH: 345
<212> TYPE: DNA
<213> ORGANISM: artificial
<220> FEATURE:
<223> OTHER INFORMATION: nucleotide sequence of the extracellular
      portion of human mutated F119SICOS

<400> SEQUENCE: 26

```
gaaatcaatg gttctgccaa ttatgagatg tttatatttc acaacggagg tgtacaaatt      60
ttatgcaaat atcctgacat tgtccagcaa tttaaaatgc agttgctgaa agggggggcaa    120
atactctgcg atctcactaa gacaaaagga agtggaaaca cagtgtccat taagagtctg    180
aaattctgcc attctcagtt atccaacaac agtgtctctt ttttttctata caacttggac    240
cattctcatg ccaactatta cttctgcaac ctatcaattt tgatcctcc  tccttctaaa    300
gtaactctta caggaggata tttgcatatt tatgaatcac aactt                     345
```

<210> SEQ ID NO 27

```
<211> LENGTH: 300
<212> TYPE: PRT
<213> ORGANISM: homo sapiens

<400> SEQUENCE: 27
```

| | | | | | | | | | | | | | | |
|---|---|---|---|---|---|---|---|---|---|---|---|---|---|---|
| Met | Arg | Leu | Gly | Ser | Pro | Gly | Leu | Leu | Phe | Leu | Phe | Ser | Ser | Leu |
| 1 | | | | 5 | | | | | 10 | | | | | 15 |
| Arg | Ala | Asp | Thr | Gln | Glu | Lys | Glu | Val | Arg | Ala | Met | Val | Gly | Ser | Asp |
| | | | 20 | | | | | 25 | | | | | 30 | | |
| Val | Glu | Leu | Ser | Cys | Ala | Cys | Pro | Glu | Gly | Ser | Arg | Phe | Asp | Leu | Asn |
| | | 35 | | | | | 40 | | | | | 45 | | | |
| Asp | Val | Tyr | Val | Tyr | Trp | Gln | Thr | Ser | Glu | Ser | Lys | Thr | Val | Val | Thr |
| 50 | | | | | 55 | | | | | 60 | | | | | |
| Tyr | His | Ile | Pro | Gln | Asn | Ser | Ser | Leu | Glu | Asn | Val | Asp | Ser | Arg | Tyr |
| 65 | | | | | 70 | | | | | 75 | | | | | 80 |
| Arg | Asn | Arg | Ala | Leu | Met | Ser | Pro | Ala | Gly | Met | Leu | Arg | Gly | Asp | Phe |
| | | | | 85 | | | | | 90 | | | | | 95 | |
| Ser | Leu | Arg | Leu | Phe | Asn | Val | Thr | Pro | Gln | Asp | Glu | Gln | Lys | Phe | His |
| | | | 100 | | | | | 105 | | | | | 110 | | |
| Cys | Leu | Val | Leu | Ser | Gln | Ser | Leu | Gly | Phe | Gln | Glu | Val | Leu | Ser | Val |
| | | 115 | | | | | 120 | | | | | 125 | | | |
| Glu | Val | Thr | Leu | His | Val | Ala | Ala | Asn | Phe | Ser | Val | Pro | Val | Val | Ser |
| 130 | | | | | 135 | | | | | 140 | | | | | |
| Ala | Pro | His | Ser | Pro | Ser | Gln | Asp | Glu | Leu | Thr | Phe | Thr | Cys | Thr | Ser |
| 145 | | | | | 150 | | | | | 155 | | | | | 160 |
| Ile | Asn | Gly | Tyr | Pro | Arg | Pro | Asn | Val | Tyr | Trp | Ile | Asn | Lys | Thr | Asp |
| | | | | 165 | | | | | 170 | | | | | 175 | |
| Asn | Ser | Leu | Leu | Asp | Gln | Ala | Leu | Gln | Asn | Asp | Thr | Val | Phe | Leu | Asn |
| | | | 180 | | | | | 185 | | | | | 190 | | |
| Met | Arg | Gly | Leu | Tyr | Asp | Val | Val | Ser | Val | Leu | Arg | Ile | Ala | Arg | Thr |
| | | 195 | | | | | 200 | | | | | 205 | | | |
| Pro | Ser | Val | Asn | Ile | Gly | Cys | Cys | Ile | Glu | Asn | Val | Leu | Leu | Gln | Gln |
| 210 | | | | | 215 | | | | | 220 | | | | | |
| Asn | Leu | Thr | Val | Gly | Ser | Gln | Thr | Gly | Asn | Asp | Ile | Gly | Glu | Arg | Asp |
| 225 | | | | | 230 | | | | | 235 | | | | | 240 |
| Lys | Ile | Thr | Glu | Asn | Pro | Val | Ser | Thr | Gly | Glu | Lys | Asn | Ala | Ala | Thr |
| | | | | 245 | | | | | 250 | | | | | 255 | |
| Trp | Ser | Ile | Leu | Ala | Val | Leu | Cys | Leu | Leu | Val | Val | Val | Ala | Val | Ala |
| | | | 260 | | | | | 265 | | | | | 270 | | |
| Ile | Gly | Trp | Val | Cys | Arg | Asp | Arg | Cys | Leu | Gln | His | Ser | Tyr | Ala | Gly |
| | | 275 | | | | | 280 | | | | | 285 | | | |
| Ala | Trp | Ala | Val | Ser | Pro | Glu | Thr | Glu | Leu | Thr | Gly |
| 290 | | | | | 295 | | | | | 300 | |

```
<210> SEQ ID NO 28
<211> LENGTH: 124
<212> TYPE: PRT
<213> ORGANISM: mus musculus

<400> SEQUENCE: 28
```

| | | | | | | | | | | | | | | |
|---|---|---|---|---|---|---|---|---|---|---|---|---|---|---|
| Glu | Ile | Asn | Gly | Ser | Ala | Asp | His | Arg | Met | Phe | Ser | Phe | His | Asn | Gly |
| 1 | | | | 5 | | | | | 10 | | | | | 15 | |
| Gly | Val | Gln | Ile | Ser | Cys | Lys | Tyr | Pro | Glu | Thr | Val | Gln | Gln | Leu | Lys |
| | | | 20 | | | | | 25 | | | | | 30 | | |
| Met | Arg | Leu | Phe | Arg | Glu | Arg | Glu | Val | Leu | Cys | Glu | Leu | Thr | Lys | Thr |
| | | 35 | | | | | 40 | | | | | 45 | | | |

```
Lys Gly Ser Gly Asn Ala Val Ser Ile Lys Asn Pro Met Leu Cys Leu
            50                  55                  60

Tyr His Leu Ser Asn Asn Ser Val Ser Phe Leu Asn Asn Pro Asp
 65                  70                  75                  80

Ser Ser Gln Gly Ser Tyr Tyr Phe Cys Ser Leu Ser Ile Phe Asp Pro
                85                  90                  95

Pro Pro Phe Gln Glu Arg Asn Leu Ser Gly Gly Tyr Leu His Ile Tyr
                100                 105                 110

Glu Ser Gln Leu Cys Cys Gln Leu Lys Leu Trp Leu
                115                 120
```

<210> SEQ ID NO 29
<211> LENGTH: 199
<212> TYPE: PRT
<213> ORGANISM: homo sapiens

<400> SEQUENCE: 29

```
Met Lys Ser Gly Leu Trp Tyr Phe Phe Leu Phe Cys Leu Arg Ile Lys
  1               5                  10                  15

Val Leu Thr Gly Glu Ile Asn Gly Ser Ala Asn Tyr Glu Met Phe Ile
             20                  25                  30

Phe His Asn Gly Gly Val Gln Ile Leu Cys Lys Tyr Pro Asp Ile Val
             35                  40                  45

Gln Gln Phe Lys Met Gln Leu Leu Lys Gly Gly Gln Ile Leu Cys Asp
         50                  55                  60

Leu Thr Lys Thr Lys Gly Ser Gly Asn Thr Val Ser Ile Lys Ser Leu
 65                  70                  75                  80

Lys Phe Cys His Ser Gln Leu Ser Asn Asn Ser Val Ser Phe Phe Leu
                 85                  90                  95

Tyr Asn Leu Asp His Ser His Ala Asn Tyr Tyr Phe Cys Asn Leu Ser
                100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
            195
```

<210> SEQ ID NO 30
<211> LENGTH: 681
<212> TYPE: DNA
<213> ORGANISM: homo sapiens

<400> SEQUENCE: 30

```
gacaaaactc acacatgccc accgtgccca gcacctgaac tcctgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
```

```
cgtgtggtca gcgtcctcac cgtcctgcac caggactggc tgaatggcaa ggagtacaag      300
tgcaaggtct ccaacaaagc cctcccagcc cccatcgaga aaaccatctc caaagccaaa      360
gggcagcccc gagaaccaca ggtgtacacc ctgcccccat cccgggagga gatgaccaag      420
aaccaggtca gcctgacctg cctggtcaaa ggcttctatc ccagcgacat cgccgtggag      480
tgggagagca atgggcagcc ggagaacaac tacaagacca cgcctcccgt gctggactcc      540
gacggctcct tcttcctcta tagcaagctc accgtggaca gagcaggtg gcagcagggg      600 aacgtcttct catgctccgt gatgcatgag gctctgcaca accactacac gcagaagagc      660
ctctccctgt ccccgggtaa a                                                681

<210> SEQ ID NO 31
<211> LENGTH: 666
<212> TYPE: DNA
<213> ORGANISM: mus musculus

<400> SEQUENCE: 31
ggttgtaagc cttgcatatg tacagtccca gaagtatcat ctgtcttcat cttcccccca       60
aagcccaagg atgtgctcac cattactctg actcctaagg tcacgtgtgt tgtggtagac      120
atcagcaagg atgatcccga ggtccagttc agctggtttg tagatgatgt ggaggtgcac      180
acagctcaga cgaaaccccg ggaggagcag atcaacagca ctttccgttc agtcagtgaa      240
cttcccatca tgcaccagga ctggctcaat ggcaaggagt tcaaatgcag ggtcaacagt      300
gcagctttcc ctgcccccat cgagaaaacc atctccaaaa ccaaaggcag accgaaggct      360
ccacaggtgt acaccattcc acctcccaag gagcagatgg ccaaggataa agtcagtctg      420
acctgcatga taacaaactt cttccctgaa gacattactg tggagtggca gtggaatggg      480
cagccagcgg agaactacaa gaacactcag cccatcatgg acacagatgg ctcttacttc      540
gtctacagca agctcaatgt gcagaagagc aactgggagg caggaaatac tttcacctgc      600
tctgtgttac atgagggcct gcacaaccac catactgaga gagcctctc ccactctcct      660 ggtaaa                                                                 666
```